United States Patent [19]
Greaves et al.

[11] Patent Number: 5,596,838
[45] Date of Patent: Jan. 28, 1997

[54] METHOD AND INSTRUMENT FOR THE PREPARATION OF POLLEN FOR CRYOGENIC STORAGE

[75] Inventors: John A. Greaves, Sheldahl; Norman P. Cloud; Martin A. Stoecker, both of Ames, all of Iowa; Raymond Russotti, Hudson, N.H.

[73] Assignee: Zenco (No. 4) Limited, London, England

[21] Appl. No.: 282,629

[22] Filed: Jul. 29, 1994

Related U.S. Application Data

[63] Continuation-in-part of Ser. No. 260,184, Jun. 15, 1994, abandoned.
[51] Int. Cl.$^6$ .............................. A01G 7/00; A01H 5/00
[52] U.S. Cl. .............................. 47/58; 426/419; 426/465; 800/200
[58] Field of Search .............................. 47/58; 426/418, 426/419, 465; 800/200

[56] References Cited

U.S. PATENT DOCUMENTS 4,746,071  5/1988  Grunhoff et al. .............................. 241/2

OTHER PUBLICATIONS

Dereuddre, J; Blandin, S; Hassen, N. "Resistance of Alginate–Coated Somatic Embryos of Carrot (Daucus–Coarota L) to Desiccation and Freezing in Liquid–Nitrogen.1. Effects of Preculture", pp. 125–134 Cryo–Letters, vol. 12, 1991.

Dereuddre, J; Gazeau, C. "Natural Frost Resistance in Plants", pp. 7–25. Bulletin de la Societe Botanique de France, Actualites Bontaniques, 133 (3), 1986.

Dereuddre, J; Scottez, C; Arnaud, Y; Duron, M. "Resistance of Alginate–Coated Axillary Shoot Tips of Pear Tree (Pyrus Communis L. CV Beurre Hardy) in Vitro Plantlets to Dehydration and Subsequent Freezing in Liquid Nitrogen: Effect of Previous Cold Hardening—Shoot Tips Culture Encapsulation in Calcium Alginate Bead; Crypreservation and Plant Propagation; Germplasm Peservation", p. 31, 7, 317–23. C. P. Seances Acad. Sci, Serial 3, 1990.

Morisset, C; Gazeau, C; Hansz, J; Dereuddre., J. "Importance of Actin Cytoskeleton Behavior During Preservation of Carrot Cell–Suspensions in Liquied–Nitrogen", pp. 35–47. Protoplasm, vol. 173, 1993.

Nirde, P; Delbos, M; Combes, D. "New Procedure for Storing Pollen at Low Temperatures", pp. 211–212. Plant Physiology and Biochemistry, 26 (2), 1988.

Barnabas, B; Kovacs, G.; Abranyi, A.; and Pfahler, P. "Effects of Pollen Storage by Drying and Deep–Freezing on the Expression of Different Agronomic Traits in Maize (Zea mays L.)", Kluwer Academic Publishers, Dordrecht— Printed in the Netherlands, pp. 221–225. Euphytica 39(3) 1988.

Collins, T. C.; Lertmongkol, V.; and Jones, J. P. "Pollen Storage of Certain Agronomic Species in Liquid Air", Crop Science, vol. 13, Jul.–Aug. 1973, pp. 493–494.

Barnabas, B Preservation of Maize Pollen Biotechnology in Agriculture and Forestry, vol. 25 Maize (ed. by Y. P. S. Bajaj) Springer–Verlag Berlin Heidelberg (1994).

Barnabas, B. "Effects of Water Loss on Germination Ability of Maize (Zea mays L.)", Annals of Botany 55, pp. 201–204, 1985.

Barnabas, B. and Rajki, E. "Fertility of Deep–frozen Maize (Zea Mays L.) Pollen" Agriculture Research Institute of the Hungarian Academy of Sciences, Annals of Botany Company (1981).

Barnabas, B. and Rajki, E. "Storage of Maize (Zea Mays L.) Pollen at –196°C in Liquid Nitrogen", Euphytica 25 (1976) pp. 747–752.

Nath, J. and Anderson, J. O. "Effect of Freezing and Freeze–Drying on the Viability and Storage of Lilium longiflorum L. and Zea mays L. Pollen", Cryobiology 12, pp. 81–88 (1975).

Daniel, L. "Retention of the Germinating Power of Pollen during Storage", Institute of Genetics of the Hungarian–Academy of Sciences, Budapest.

Connor, Kristina and Towill, Leigh. "Pollen–Handling Protocol and Hydration/Dehydration Characteristics of Pollen for Application to Long–Term Storage", Kluwer Academics Publisher 1993 pp. 77–84.

Walden, D. B. "Male Gametophyte of Zea mays L." Crop Science, vol. 7, Sep.–Oct. 1967 pp. 441–443.

Shands, H. L.; Janisch, D. C.; and Dickson, A. D. "Germination Response of Barley Following Different Harvesting Conditions and Storage Treatments." Crop Science, vol. 7, Sep.–Oct. 1967.

Barnabas et al (1984) Acta Bot. Hung 30 (3–4):329–332.

Primary Examiner—Douglas W. Robinson
Assistant Examiner—Elizabeth F. McElwain
Attorney, Agent, or Firm—Dana Rewoldt

[57] ABSTRACT

The present invention relates to a method and instrument for the preparation of pollen and the development of a pollen bank for breeding purposes. More specifically, the invention relates to a method and instrument that permits pollen to be cryogenically stored in a viable state. Specifically, the present invention relates to a method of employing a heat or water or pressure related measurement to determine the readiness of the pollen for cryogenic storage.

17 Claims, 21 Drawing Sheets

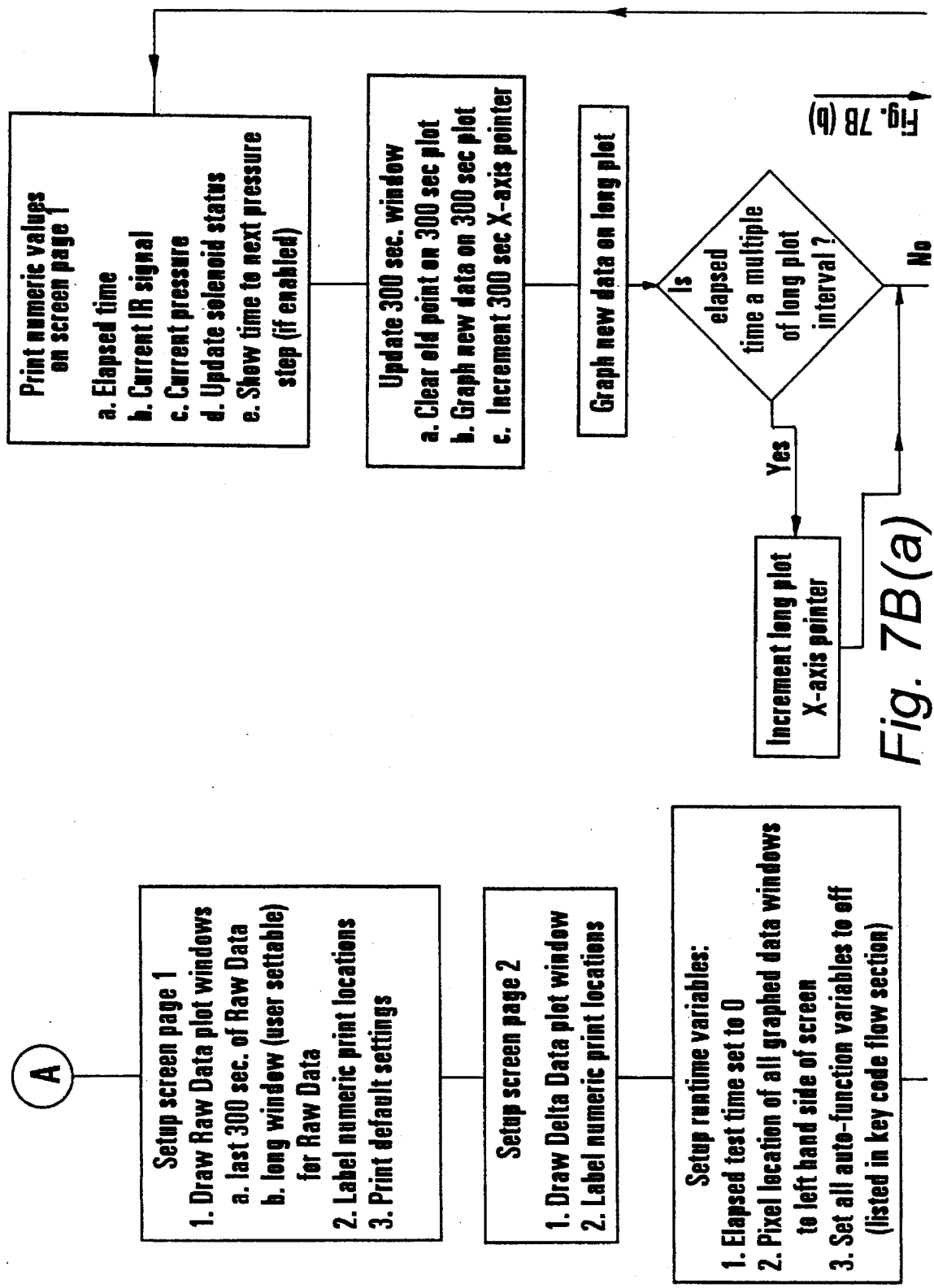

METHOD AND INSTRUMENT FOR THE PREPARATION OF POLLEN FOR CRYOGENIC STORAGE

This application is continuation-in-part of U.S. patent application No. 08/260,184 filed on Jun. 15, 1994 now abandoned.

FIELD OF THE INVENTION

The present invention relates to a method and instrument for the preparation of pollen and the development of a pollen bank for breeding purposes. More specifically, the invention relates to a method and instrument that permits pollen to be cryogenically stored in a viable state. Specifically, the present invention relates to a method of employing a heat or water or pressure related measurement to determine the readiness of the pollen for cryogenic storage.

BACKGROUND OF THE INVENTION

Plant breeding is one of the oldest recorded accomplishments of mankind. The ability to breed plants is an important mark in man's movement from nomadic life to organized society. Today's food crops are essentially the result of mankind's primitive plant breeding attempts.

The practice of plant breeding has progressed to a science. Plant breeding became a science when genetic principles gave predictability to plant breeding. Plant breeding is basically man's conscious selection of genetic material instead of nature's selection of genetic material. Examples of the successes of plant breeding are the increased productivity of field crops, development of insect resistant crops and disease resistant crops. The progression of the plant breeding science has been slowed by natural factors. These factors include: the length of time necessary for development of a plant to its sexual maturity, the length of time to pollen viability and the length of time to maturity of the pollen receptor. Presently plants, specifically maize, can only be pollinated when a plant is sexually mature, pollen is viable, and pollen receptors are available. Thus, if plants are cross pollinated such that the pollen of one plant is used to pollinate a second plant, the sexual maturity of both plants have to be coordinated to permit pollination to occur as the time period of pollen viability is limited in most crops. One proposed method of increasing the efficiency and speed of plant breeding is to develop a system of storing pollen in a viable condition, a pollen bank. This would eliminate the need to coordinate the timing of sexual maturity of two plants and effectively eliminate one of the time factors in the plant breeding process. It eliminates plant breeding problems such as when pollen shed does not coincide with receptor maturity. Furthermore, a long term storage of viable pollen would provide an unique ability to conserve and manipulate genetic resources. The ability to retrieve viable pollen, obtained from an individual plant stored for long periods of time would provide great flexibility in plant breeding programs. Furthermore, in today's present environment of plant breeding research a pollen storage system provides a method to expand restrictive fragment length polymorphism research and transgenic biotechnology breeding programs by creating a germplasm bank of pollen which can be fingerprinted for future use in breeding programs.

Methods for storage of viable pollen have been tested and some pollen can be stored. However, pollen from many row crops, especially maize, has not been successfully stored. Research on maize pollen storage has shown some limited success using air flotation when large quantities of pollen are stored. An air flotation method of drying prepares maize pollen for medium to long term storage. The system is somewhat limited as it does not allow the stored pollen to be readily used in a commercial breeding program. The air flotation dries large quantities of pollen for storage. This stored pollen often has less than acceptable levels of viability when employed. This makes the use of stored pollen on a commercial basis unsatisfactory. There remains a need for a method and instrument for preparing pollen for individual plants which can be used and stored for use in research and commercial breeding programs. There remains a need for a method and instrument which can determine when pollen is properly prepared so that the pollen will be viable after storage in liquid nitrogen.

SUMMARY OF THE INVENTION

An object of the present invention is to provide a unique method of plant breeding employing viable stored pollen.

A further object of the present invention is to provide a method for preparing pollen for storage such that the pollen remains viable.

Another object of the present invention is to provide a device which prepares pollen for viable storage.

Yet another object of the present invention is to provide a device which prepares pollen to be stored in a germplasm bank.

Additionally, another object of the present invention is to provide a method of preparing pollen, storing pollen and categorizing pollen to form a germplasm bank of viable pollen.

Yet, still another object of the present invention is to provide a device which accurately senses the correct level of pollen moisture for viable storage conditions.

Still another object of the present invention is to provide a method for preparing pollen for storage, storing the pollen in a viable state, and then using the stored viable pollen for pollination. A method of preparing pollen for storage comprising the steps of: (a) selecting pollen having a first moisture level; (b) exposing the pollen having the first moisture level to reduced atmospheric pressures; (c) reducing the first moisture level of the pollen to a second moisture level; and (d) storing in storage the pollen having the second moisture level. This method can include the step of monitoring the temperature of the pollen to determine when the first moisture level has been reduced to the second desired moisture level. The invention can have a temperature monitoring device to determine the moisture levels. This monitoring is done by a heat sensitive detector. More specifically, the heat sensitive detector is an infrared detector that detects temperature by sensing the infrared rays.

The method requires reduced atmospheric pressure; these reduced atmospheric pressures range between approximately 5 torr and 30 torr. The preferred range is 12 torr to 20 torr. Additionally, the method including the step of reducing the atmospheric pressures to a first pressure for a selected first time period and decreasing the atmospheric pressure from the first pressure to a second pressure for a selected second time period. Generally then, this is a method wherein the first pressure is not more than 45 torr and the second pressure is not more than 25 torr. The pressure level is pulsed; in other words, the pressure level is systematically reduced and repressurized at selected time intervals. After the pulses, the method includes the steps of removing the pollen from the storage and using the pollen. Additionally, the method can include the steps of: (e) identifying a plant source of the pollen in storage; and (f) categorizing the pollen in storage.

Broadly then the invention includes a method in which the step of repeating steps a–f (above) forms a germplasm bank containing pollen which can be used to pollinate. The present invention includes a germplasm bank adapted to maintain a variety of germplasm therein, the bank comprising: a cryogenic device adapted for storage of cryogenically preserved deposits; deposits placed within the cryogenic device and at least some of the deposits being cryogenically preserved pollen from source plants, at least some deposits of pollen being from individual source plants; and an identifying system associated with the deposits, the identifying system having symbols which identify the individual source plants of each of the deposits whereby deposits of pollen from individual source plants can be stored until the identified deposit is needed and retrieved by reference to the designated symbol.

The invention additionally includes an instrument for the preparation of pollen for storage in a viable state in a cryogenic environment, comprising: a chamber adapted to contain a pollen sample therein; and an evacuation system adapted to be connected to the chamber whereby the evacuation system causes reduced atmospheric pressure in the chamber. Additionally, the instrument can include a sensor associated with the chamber adapted to indicate when the pollen sample is prepared for storage in a viable state, whereby the pollen may be removed from the chamber and placed in storage in a cryogenic environment.

More specifically the instrument includes a chamber interior at an atmospheric pressure and the evacuation system includes a pressure control box including solenoid control valves adapted to change the atmospheric pressure of the interior of the chamber. Specifically, three solenoid control valves can be employed. Two of the solenoid control valves in the pressure control box each include a needle valve, the needle valves being adjustable, wherein the atmospheric pressure within the interior of the chamber can be changed at selected intervals. One of the solenoid control valves in the pressure control box includes an adjustable needle valve adapted to permit gradual repressurization of the interior of the chamber. The computer interface unit is operational regardless of the chambers pressure. The computer having the capability of monitoring the evacuation system.

Additionally, the present invention includes a sensor which senses heat, by detecting infrared radiation within the chamber. The thermopile (commercially available from Dexter Research Center, Inc., Dexter, Mich.) is located proximate to the sample within the chamber. The sensor is connected to a sensor computer interface unit, the sensor computer interface unit is adapted to be associated with a computer, so that the computer records the level of infrared radiation present inside the chamber as detected by the thermopile. An 8–13 um band pass filter is fitted on the thermopile to limit its response to far infrared band emissions.

A variety of other objects of the present invention are more readily appreciated and clearly understood when the following detailed description of the embodiments of the present invention are considered together with the accompanying drawings.

DETAILED DESCRIPTION OF THE EMBODIMENTS

Detailed description of the preferred embodiment of the present invention relates to an apparatus and a method useful in the preparation of pollen for long term storage in a viable state. This apparatus and method is particularly useful for cryogenic preparation of maize pollen. Furthermore with slight modifications this invention can be used to preserve seed, ovum and other biological materials without undue experimentation. The apparatus is intended to remove excess water from pollen samples by vacuum evaporation. At the correct level of dryness, i.e. removal of excess water from the pollen to a defined relative water content, the pollen can be exposed to −196° C. and be viable when thawed. After the pollen is stored, it can be rapidly thawed and rehydrated for use in pollination. This type of regular, consistent preservation of maize pollen from single tassels is heretofore undiscovered. Likewise, a maize germplasm bank formed of this pollen or other cryogenically prepared plant parts has heretofore been impossible to achieve on an individual plant level, specifically a bank for maize pollen.

Figure 1:
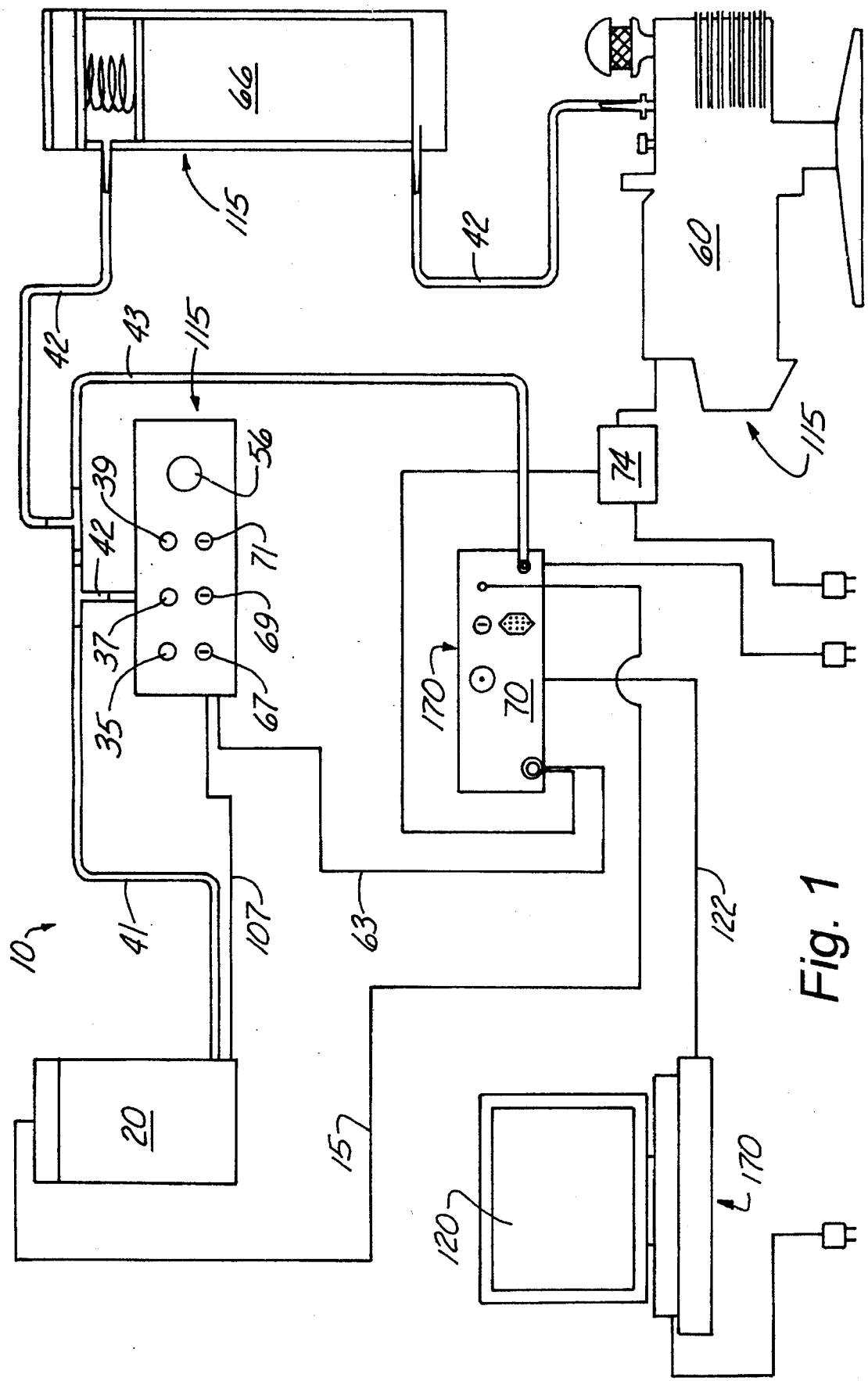
FIG. 1 is a front view of the apparatus according to an exemplary embodiment of the present invention in which the apparatus is used to perform the preferred method of the present invention.
Figure 2:
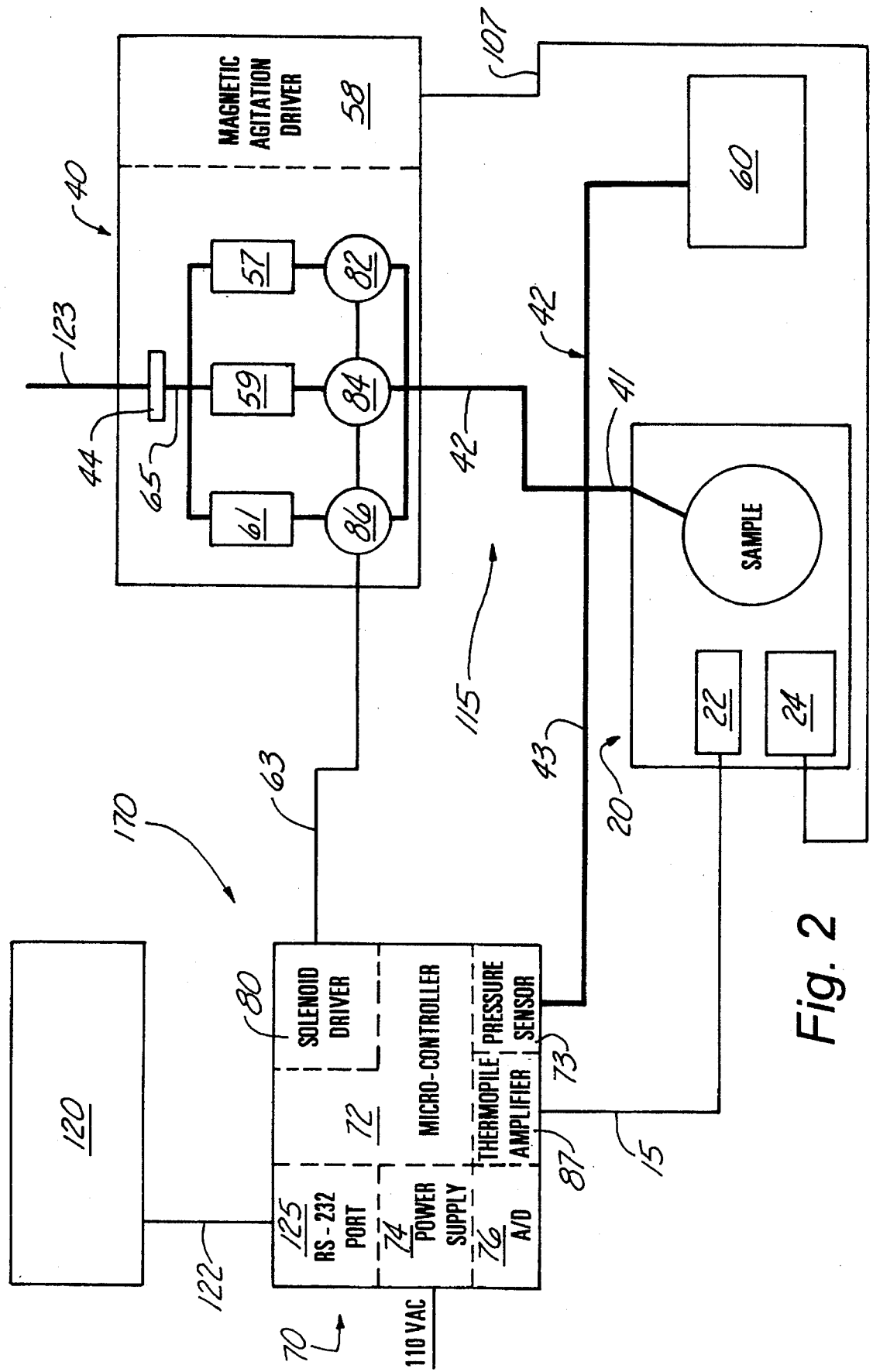
FIG. 2 is a diagram of the apparatus according to the exemplary embodiment in FIG. 1.

The broad aspects of the apparatus of the present invention are shown in FIGS. 1 and 2. In FIG. 1 there is shown a diagram of the apparatus 10 includes a sample chamber 20, a vacuum system 115, and a temperature sensor 22 (see FIG. 2). The vacuum system 115 and the temperature sensor 22 are connected to a computer system 170. The sample chamber 20 is adapted to receive a pollen sample which can be prepared for cryogenic preservation by removal of pollen moisture by pressure evacuation. The computer system 170 controls the vacuum system 115. The vacuum system 115 is adapted to evacuate sample chamber 20 to reduced atmospheric levels which in turn reduces the pollen moisture. The reduction of pollen moisture is monitored by the temperature sensor 22. The temperature sensor 22 readings are received by the computer system 170 and displayed for the operator when requested. When the pollen reaches the selected level of moisture the prepared pollen can be identified and cryogenically stored in a germplasm bank for pollination use at a future time.

The present invention has three primary units: the vacuum system, the sample chamber and the computer system. The interaction between the sample chamber 20, the vacuum system 115, and the computer system 170 is best depicted in FIG. 2. Like FIG. 1 the thick bold lines show the vacuum and the thinner lines depict electrical lines. Each of the three primary units includes one of the following three components, the computer interface unit 70, the pressure control box 40, and the sample chamber 20. A standard vacuum pump 60 and standard computer 120 were also used. The computer interface unit 70 houses all the electrical components. The pressure control box 40 houses gas solenoid control valves 82, 84, 86, needle valves 57, 59, 61, and a filter 44 for incoming air. Electrical cables and vacuum lines run between all three elements of the system as well as to the computer 120 (cables only) and vacuum pump 60. Cable shielding was used on the thermopile signal. The sample chamber 20 is grounded directly to the thermopile amplifier circuitry housed within the computer interface unit 70.

The vacuum system 115, includes a vacuum pump 60 which is connected by vacuum line 42 to a desiccator 66 which is connected by vacuum line 42 to a pressure control box 40 in an exemplary embodiment of the present invention. The pressure control box 40 (also called the gas control unit) has a port 110 on to which the vacuum line 42 is connected. The vacuum line 42 has two vacuum line segments 41, 43 which are connected through a T joint to the sample chamber 20 and the computer interface unit 70 of the computer system 170, respectively. These vacuum lines 41, 42, 43 connect vacuum system 115 to the computer system 170 and the sample chamber 20. The invention is activated by connection with power source 74. When activated the evacuation of sample chamber 20 by the vacuum system 115 is monitored and controlled by the computer system 170.

Figure 5A:
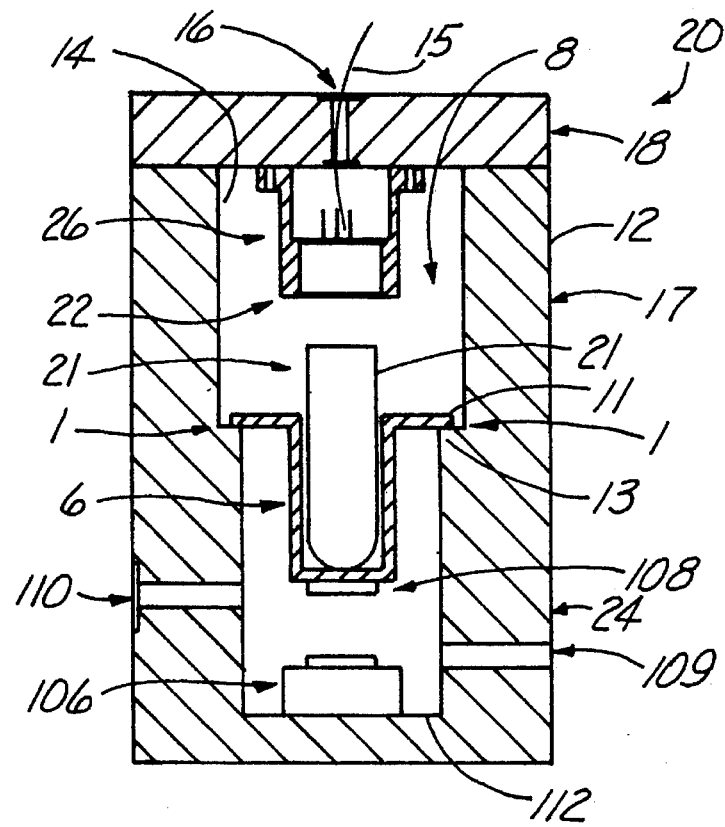
FIG. 5 is a side view of the cross section of the sample chamber of the present invention.
Figure 5B:
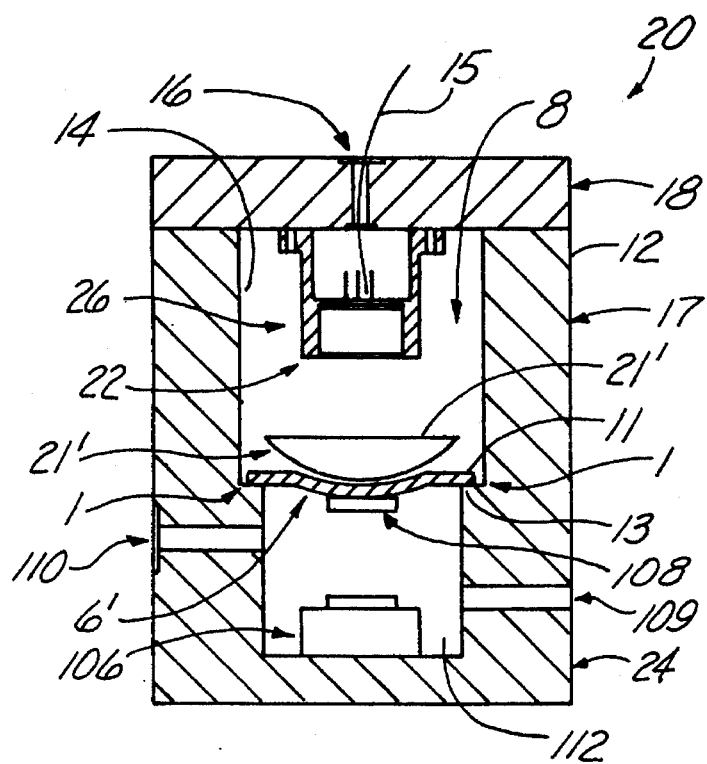

The main component of vacuum system 115 is pressure control box 40 which performs two distinct functions. One function is pressure related. The second function is not pressure related. The first function of the pressure control box 40 is to magnetically agitate the pollen sample within the sample chamber 20 (see FIG. 5). One adjustment valve depicted on the face of the pressure control box 40 is a speed control adjustor 56 for the magnetic agitator drive 56 which powers the magnetic agitator within the sample chamber 20. The agitation by the magnetic agitator avoids uneven release of moisture from the pollen sample when the sample chamber 20 is evacuated. The magnetic agitator may increase the temperature within the sample chamber 20, thus creating unwanted stress on the sample pollen. Another option to having the magnetic agitator within the chamber is to have the magnetic agitator outside of the sample chamber 20. Other alternatives include physical agitation of the entire sample chamber 20, or placing the sample pollen in a single pollen layer on a sample receptor formed as a rectangular platform having a lid. The lid avoids pollen dispersion within the chamber due to evacuation. The present invention has a dish shaped sample receptor 21.

The second function of the pressure control box 40 is to flux or pulse the pressure level in the sample chamber 20. The pressure control box 40 has three light emitting diodes 35, 37, 39 each responsive to a respective solenoid control valves. Each of the three gas solenoid control valves 82, 84, 86 have an associated needle valve which can be manually adjusted by a first needle valve adjuster 67, a second needle valve adjuster 69, a third needle valve adjuster 71, respectively. These needle valve adjusters 67, 69, and 71, permit the pressure flux or pulse change in the sample chamber 20 to be adjusted. The pressure can be deceased or increased. Additionally the length of the pressure pulse can be adjusted and the length of time between pulses can be adjusted.

Figure 3:
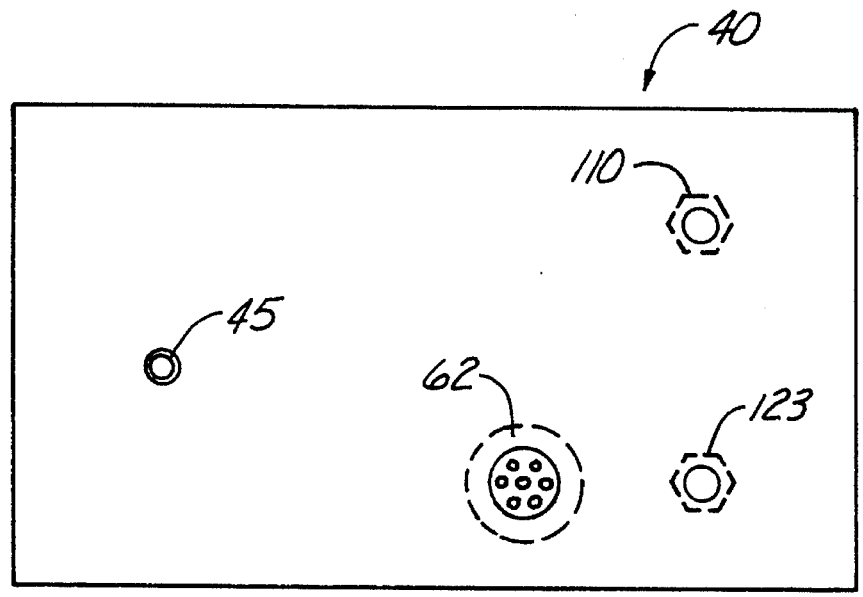
FIG. 3 is a back view of the pressure control box.

FIG. 3 shows the backface of the pressure control box 40. The magnetic shaker drive outlet 45 is connected by wire 107 into sample chamber 20. The solenoid control valves connector 62 is connected by connecting line 63 to the computer interface unit 70 and thus to the computer system 170. The vent 123 located proximate particle filter 44 permits adequate airflow and opens the solenoid control valves chambers to the atmosphere.

Figure 4:
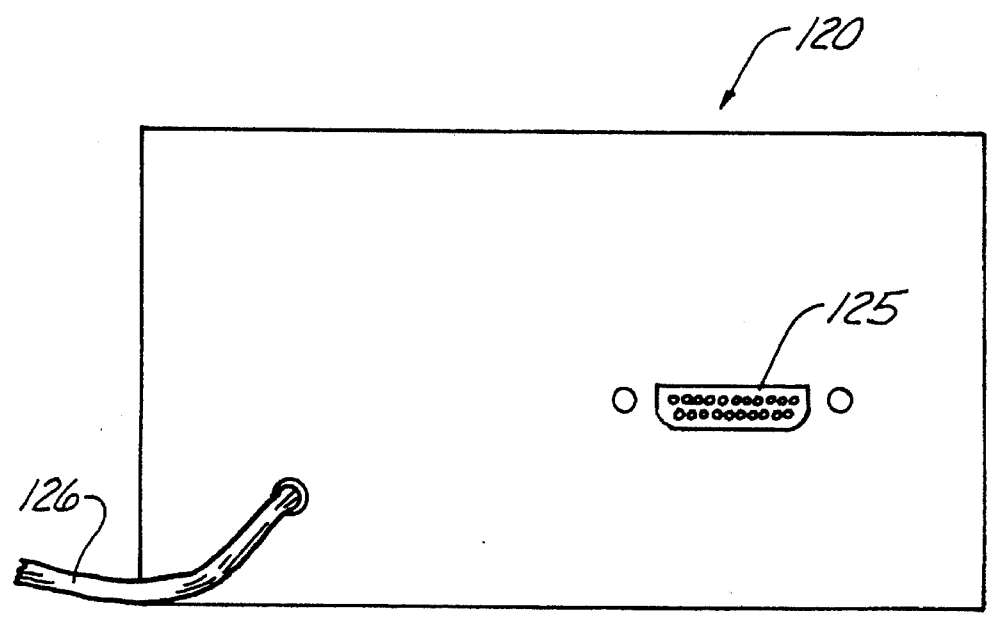
FIG. 4 is a back view of the computer interface unit.

Turning to FIGS. 1–2 & 4, these figures show the computer interface unit 70 which contains a solenoid control valves driver 80, a micro-controller 72, a RS-232 Port 125, a power supply 74, a pressure sensor (vacuum gauge) 73, a thermopile amplifier 87, and a power cord 126 which is 110 volt and connects to a power source. The solenoid control valves driver 80 is connected to the three gas solenoid control valves 82, 84, 86 in the pressure control box 40. As shown in FIGS. 3 & 4, the RS-232 Port 125 is connected by serial link 122 to the computer 120. The power supply 74 is connected to the 100 VAC. The pressure sensor 73 is connected to the sample chamber 20, the pressure control box 40 and the vacuum pump 60 by the vacuum lines 41, 42, 43.

Turning to the micro-controller 72 in the computer interface unit 70, the micro-controller interfaces for the host computer 120. The data monitoring and chamber 20 activity is controlled by computer 120. The computer system allows for ease of use. Random data information is transferred between the host computer 120 and the computer interface unit 70 via the serial link 122. Control software allows the micro computer to act as an intelligent remote peripheral with respect to the host computer 120.

Turning to the data acquisition system 76, within the computer interface unit 70 a four channel twelve bit analog to digital converter within the data acquisition system 76 gathers data from the thermopile amplifier 87 and pressure sensors 73. The amplification circuitry for the sensors is housed within computer unit 70. Adjustment of both amplifier systems "Zero" and "Gain" levels are provided within computer unit 70. Amplification circuitry is well known to those skilled in the art. An AC line frequency notched filter is placed in the thermopile amplifier 87. The AC line notched filter was employed because of the location of the sensor and the high gain required, approximately 2,000–8,000. A number of the micro-computers digital output bits are used with appropriate buffering to switch the gas solenoid control valves 56, 58, and 60, the magnetic agitator 24 and the vacuum pump 60.

Control software was written to interface with the computer 120 and the computer interface unit 70. This software could be changed and would be within the purview of those skilled in the art of writing software. The software was adapted to provide graphic and numerical displays of current sample temperature and chamber pressure and graphs for elapsed test pressure and temperature readings. A graph showing the relative amplitude of temperature variations with this pressure step can also be displayed. A variety of other graphic and numerical displays could readily be displayed depending on the criteria and spec of the software. The software is adapted to allow the user to manually switch the pump and valve combinations. There is also a separate feature which allows the computer to do various pressure levels at repeated intervals. The data is logged to the hard drive of the computer automatically by the program. A data logging frequency may be selected at the start of a test along with the run time and pressure control variables.

Figure 6:
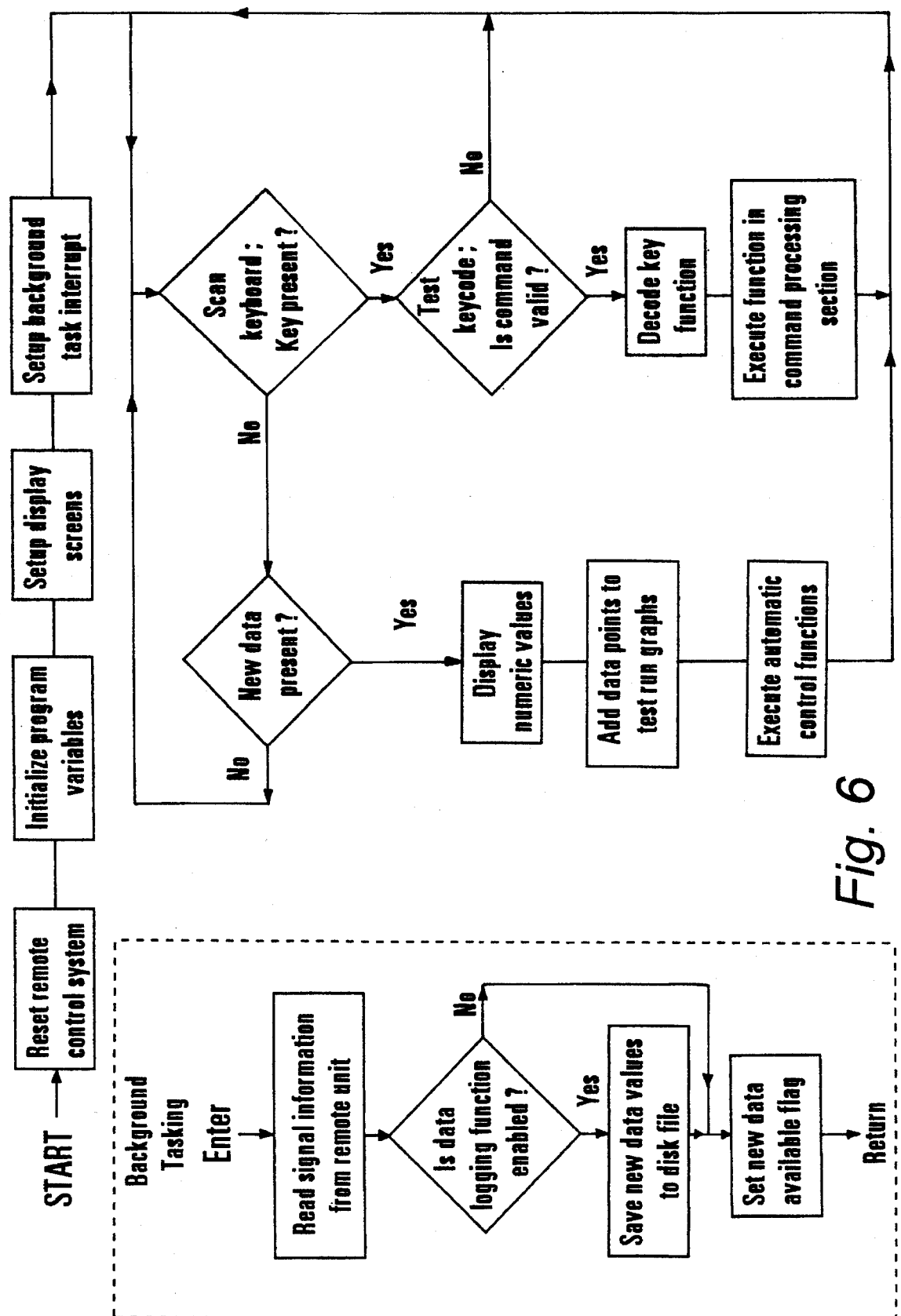
FIG. 6 is a brief flow chart of the software of the present invention.
Figure 7A:
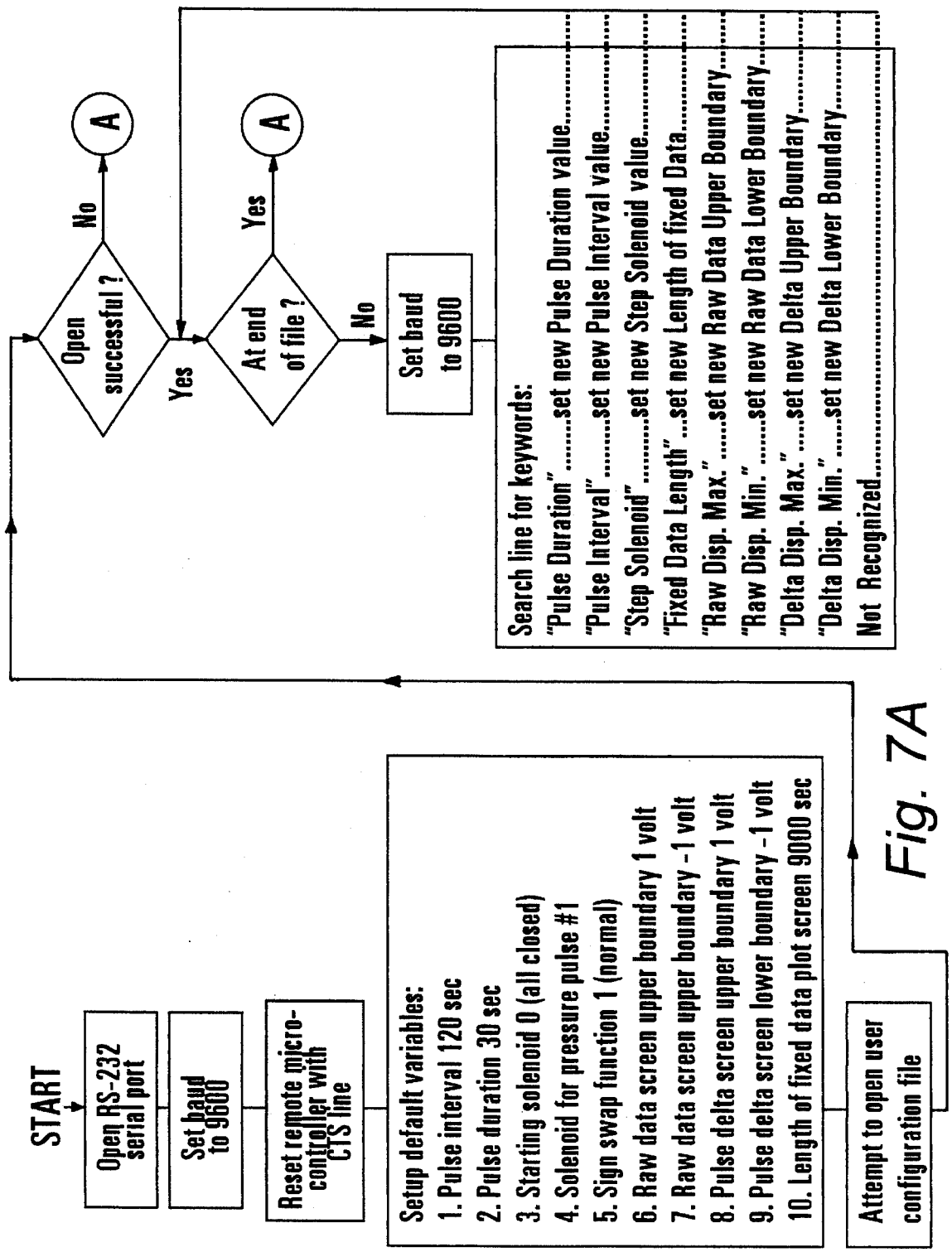
FIG. 7A–7F is a detailed flow chart of the software of the present invention.
Figure 7B:
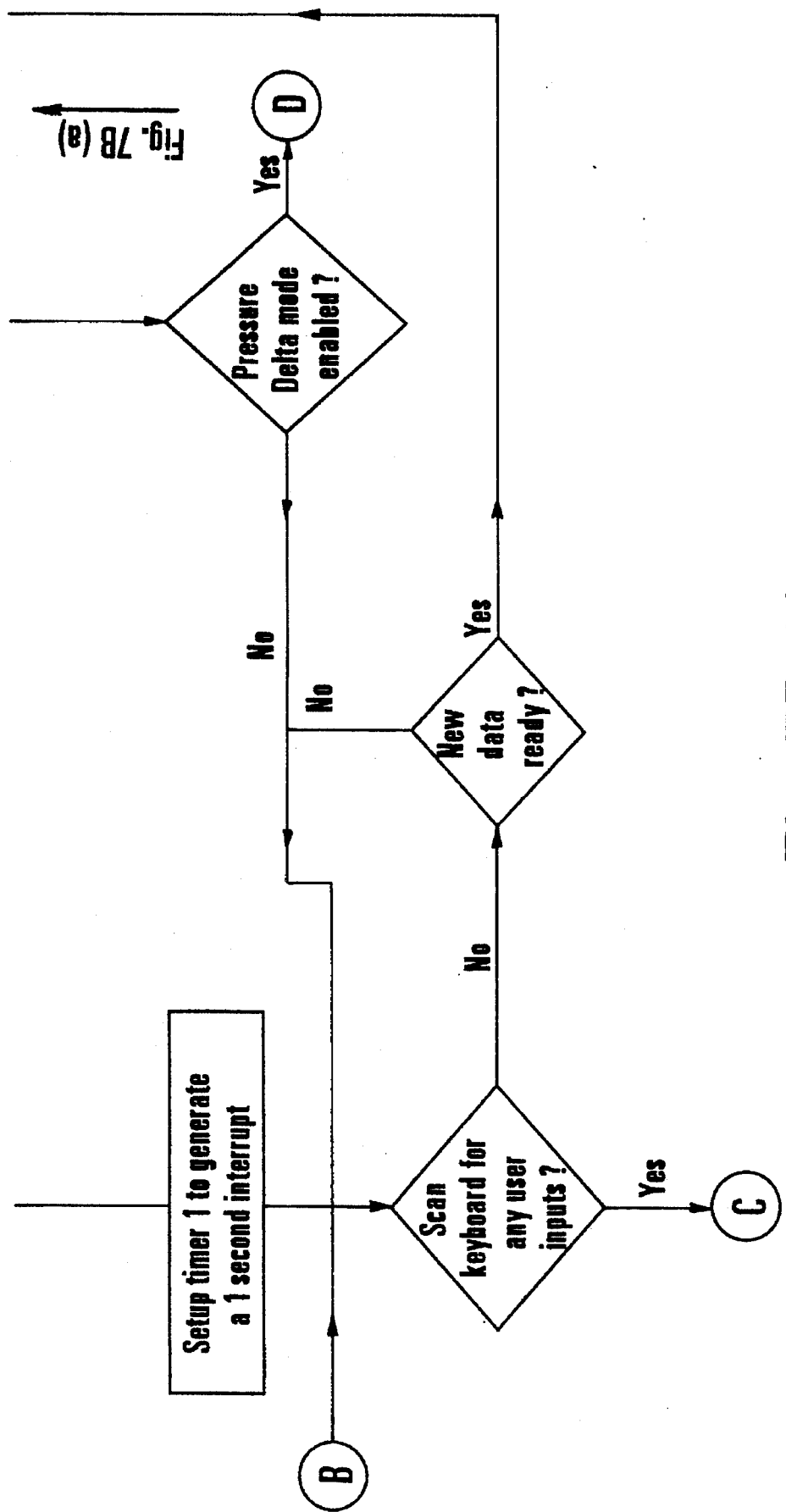
Figure 7C:
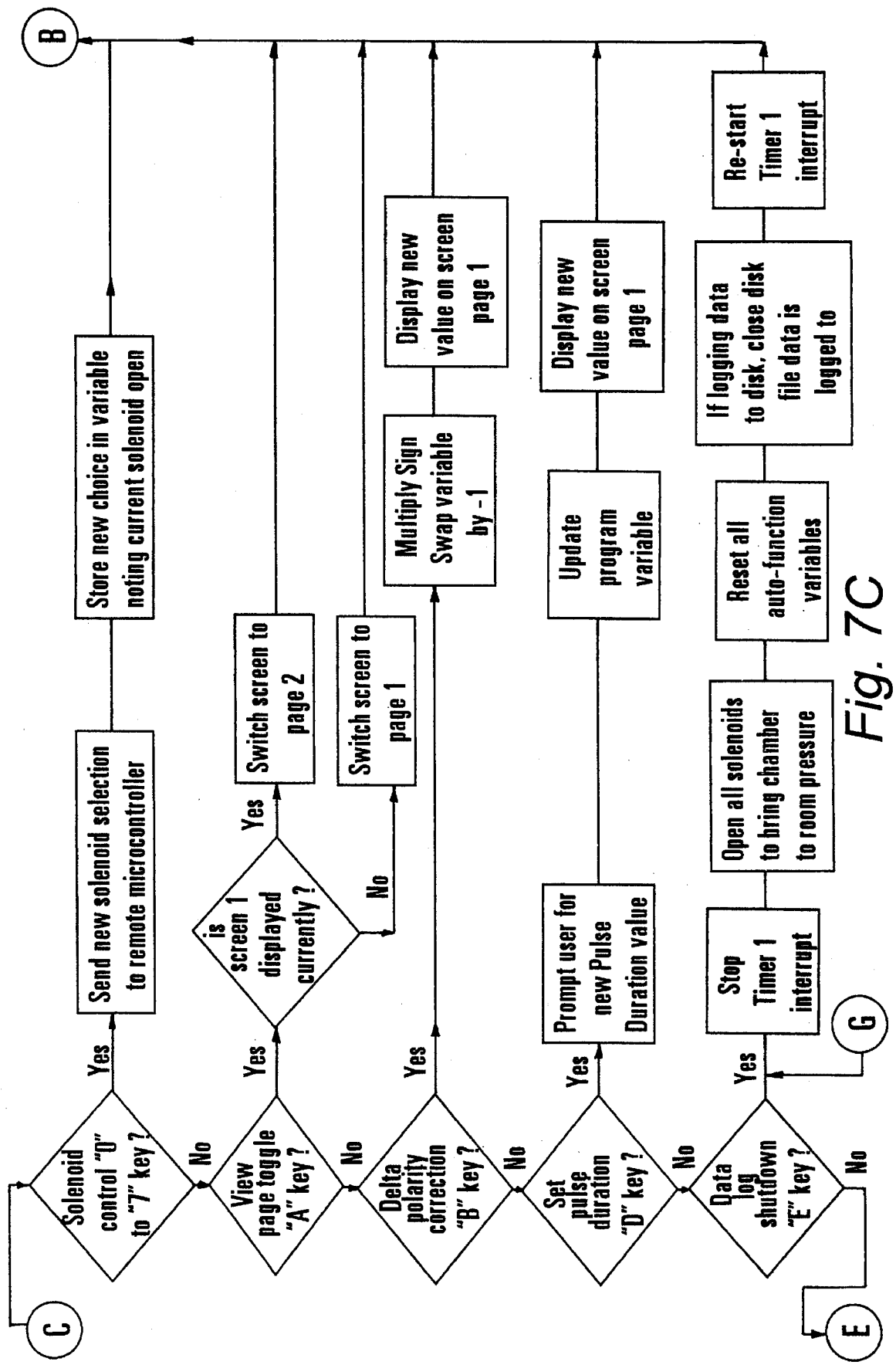
Figure 7D:
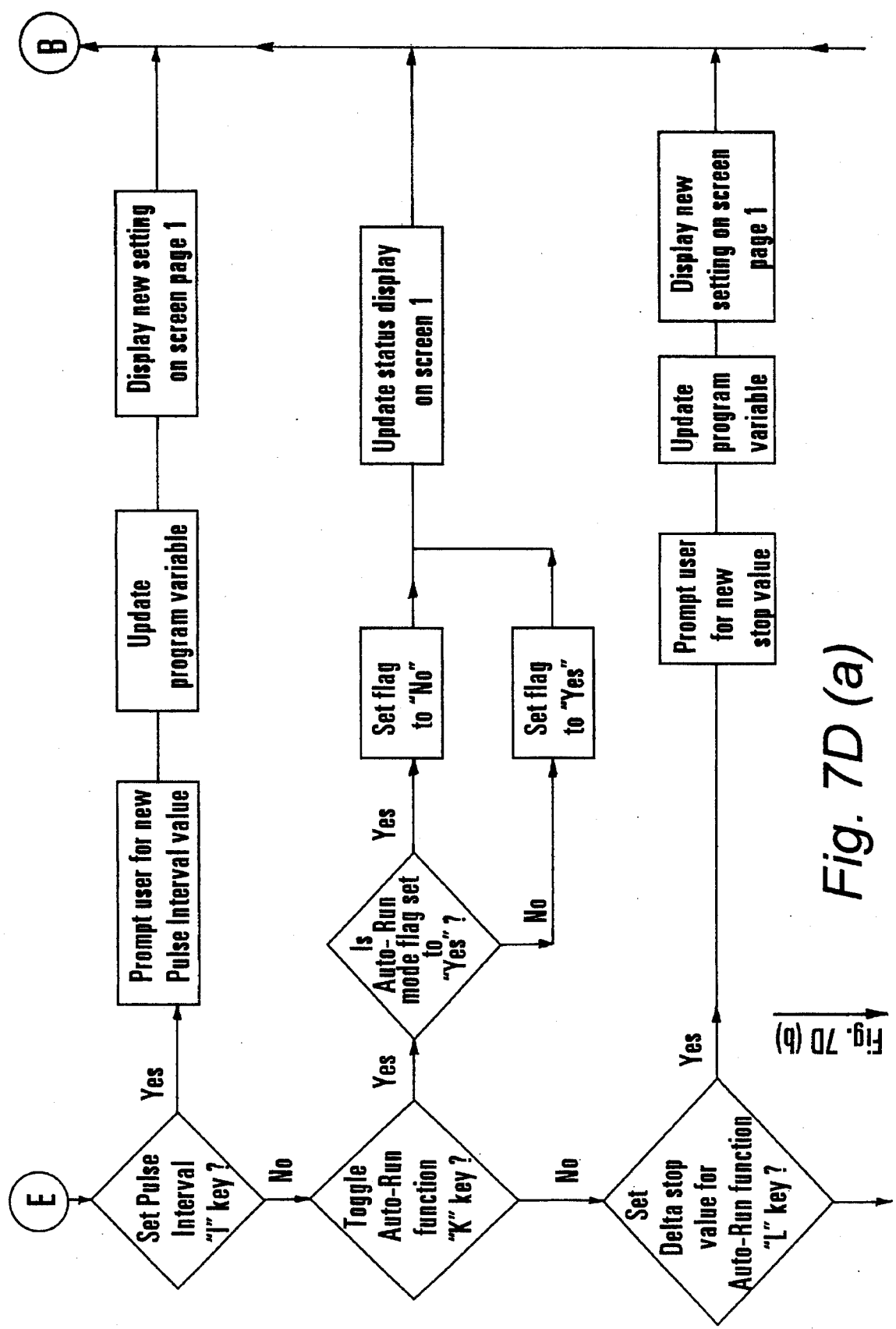
Figure 7D:
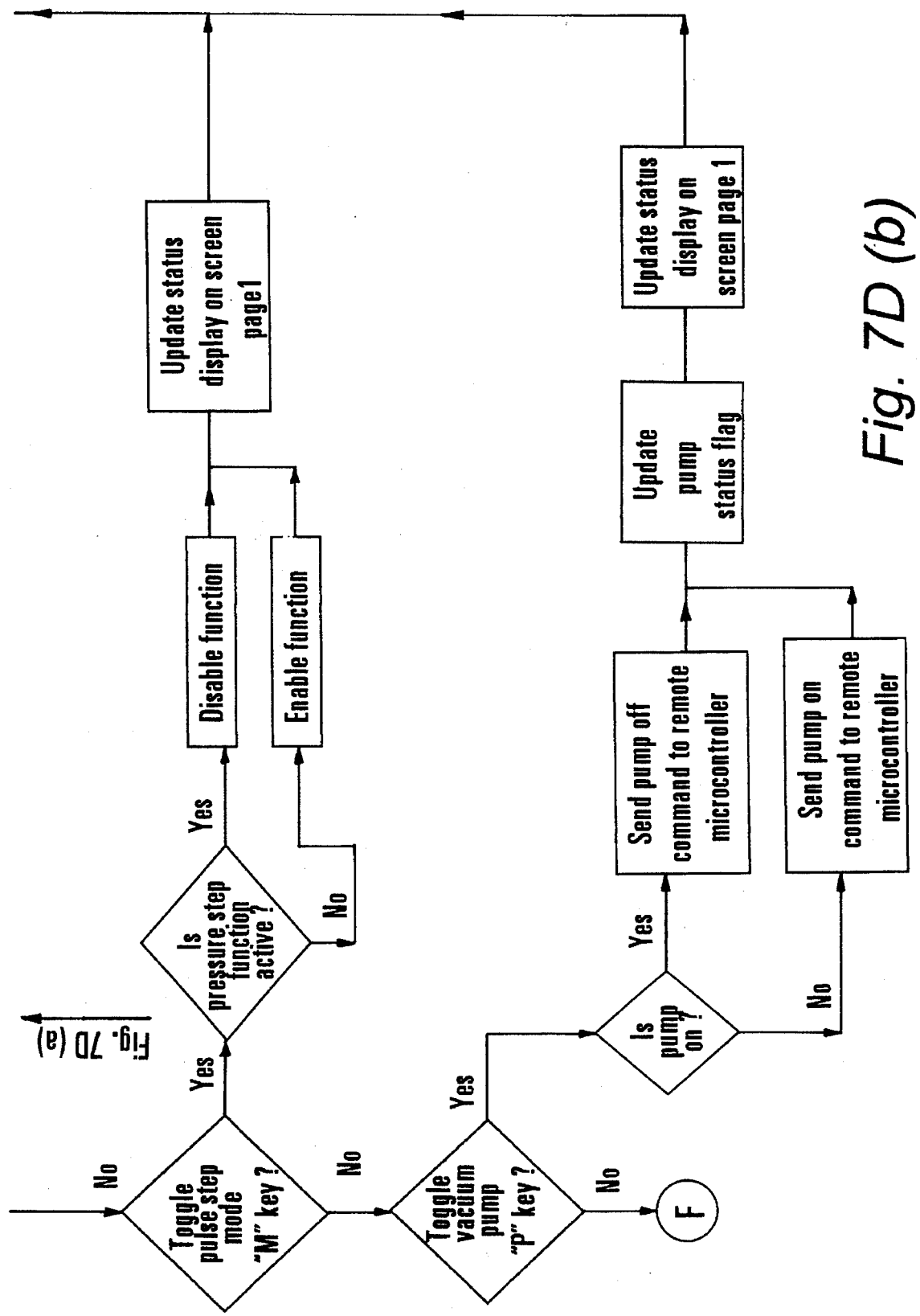
Figure 7E:
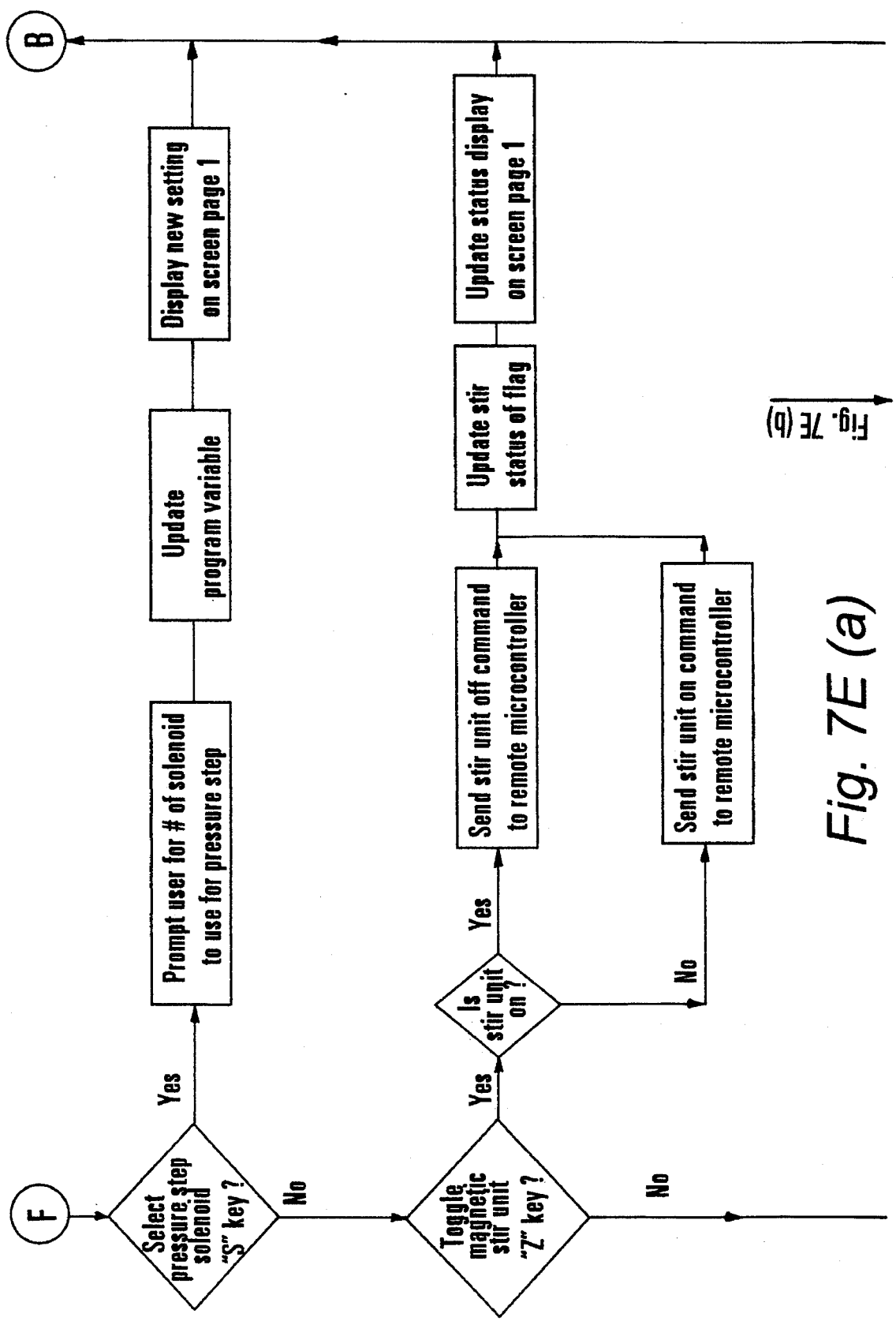
Figure 7E:
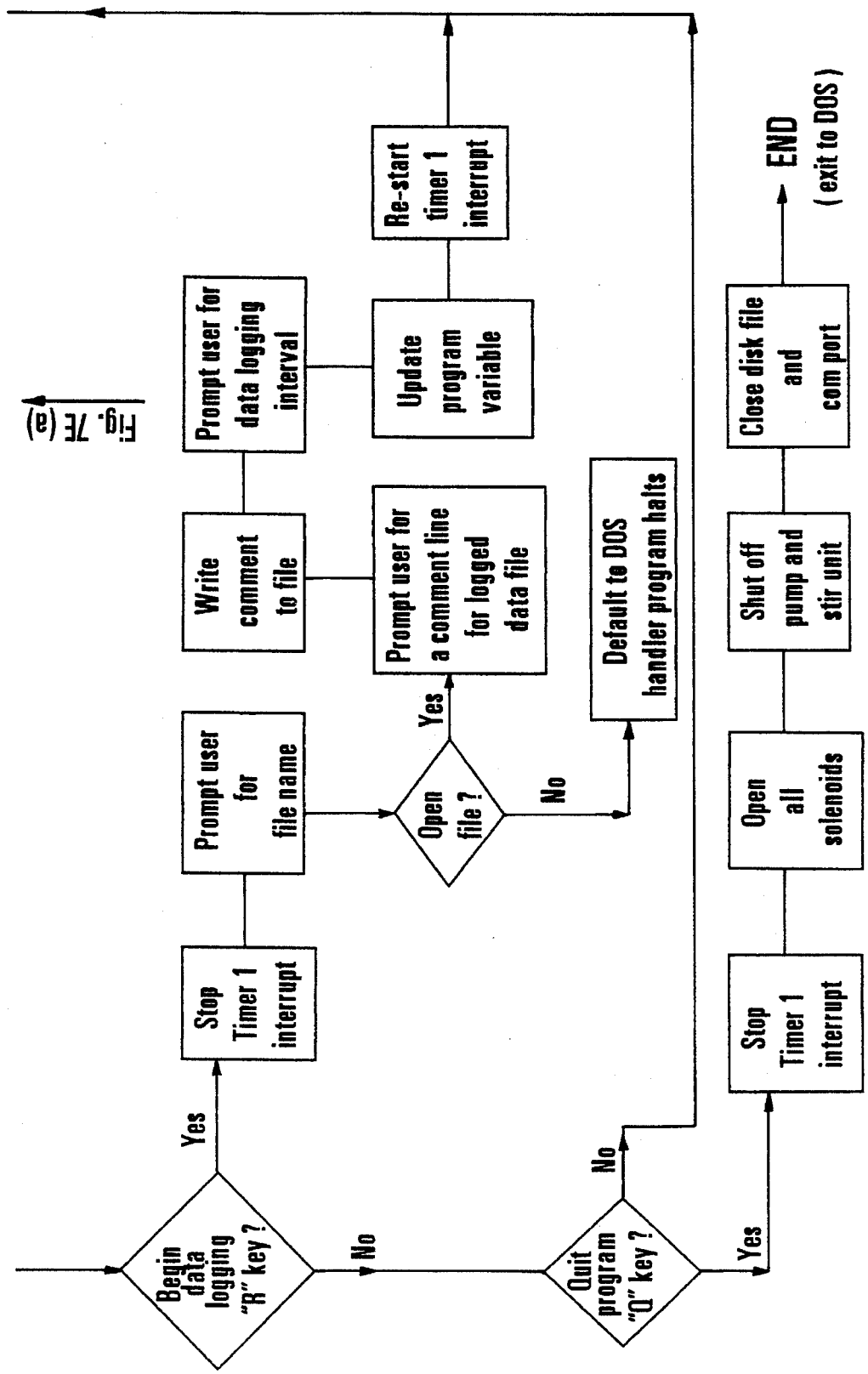
Figure 7F:
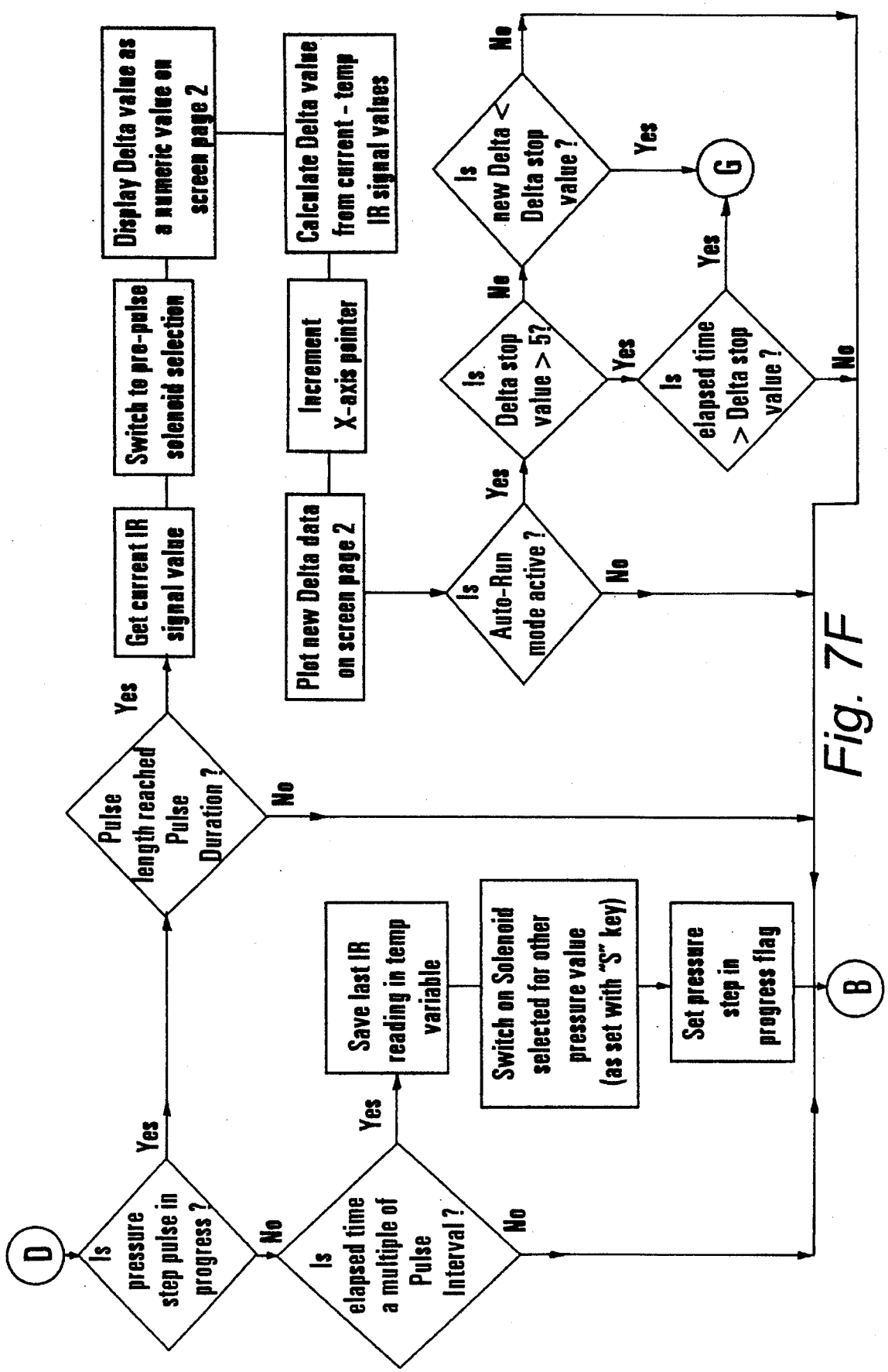
Figure 7B:
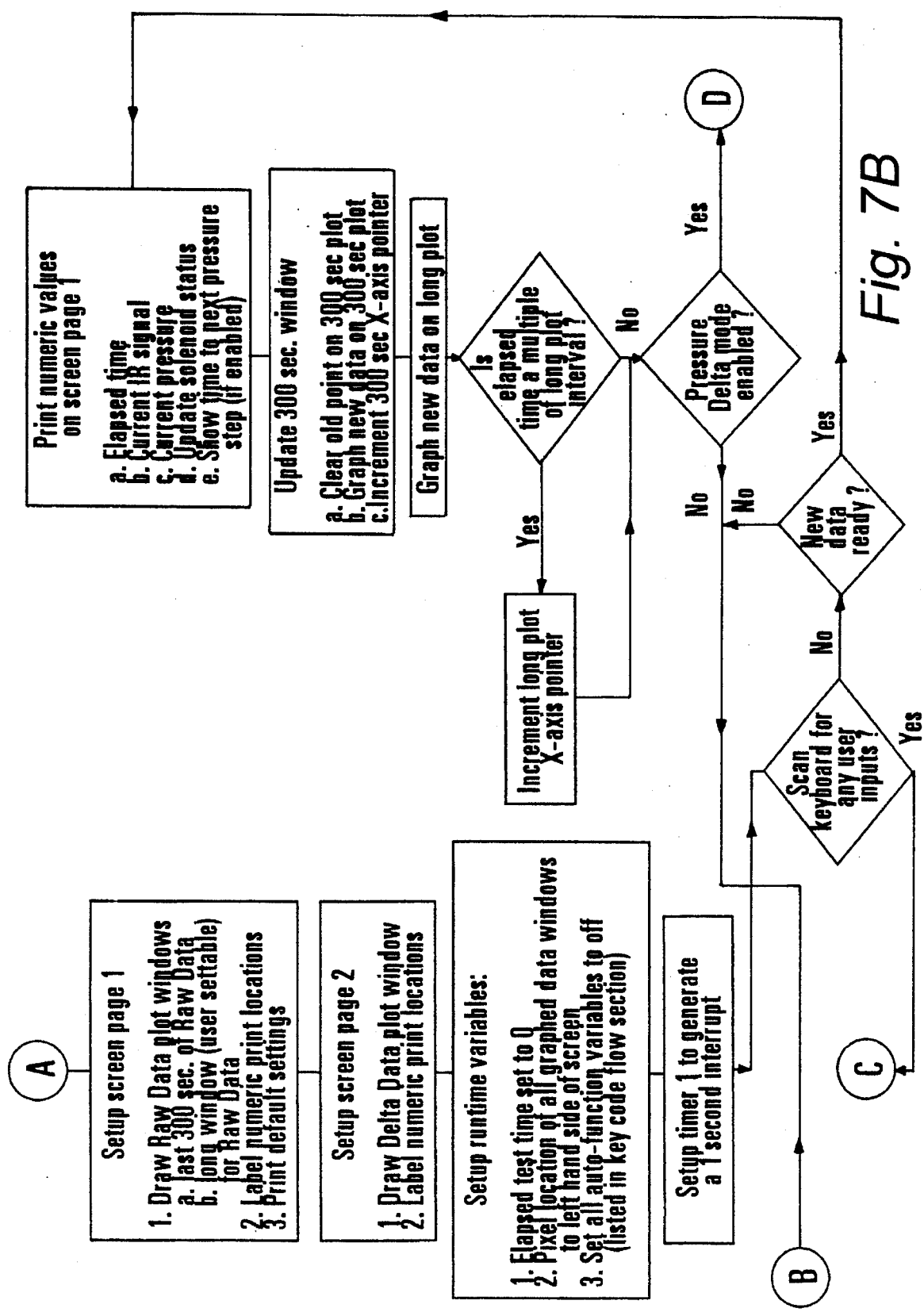

Turning to FIG. 6, the operation of the software controlling the present invention is described in broad terms. The software begins by initializing the working variables. The working variables control program operating parameters and are more clearly depicted and listed in FIG. 7. The data display screens are setup next. These screens display the acquired data in real-time numeric and graphical formats that facilitate the interpretation of the sample condition during a test run. A software reset signal is sent to the remote interface unit to place it in a known state. Making it ready to receive commands from the host system. A one second sampling interrupt is enabled in the host system. All remote data sampling is done at the occurrence of one of these interrupts and is in fact a background task. Data logging (to disk) is also executed from this part of the program. The main loop of the program is concerned with data display, user interface, and automated control of test conditions. Having the data collection running as a background task insures accurate sampling intervals with a minimum level of code complexity. The program spends most of its time awaiting real-time data and user input from the keyboard. When new data is received from the interrupt routine, it is taken and displayed numerically then graphed on one or several of the run-time graphic displays. The keyboard is periodically scanned for user command requests. Invalid entries are ignored as the program loops between checking for new data and user key inputs. The input of a valid command will result in control of the program being passed to the "command processing routine". This routine contains functions relevant to the control of test parameters and data storage.

A Detailed Description of Program Function

The lettered circles are meant to be flow continuations across multiple pages, their location was dictated by physical convenience or need as the diagramming of the program flow was done. They are not meant to be directly related to specific steps in the program cycle.

System Initialization

All communications with the test hardware is done from the host through as RS-232 serial port. The first tasks of the software are to open such a port and issue a reset command to the test hardware's computer interface unit.

Next, variables concerned with the operation conditions used for a test run are setup from hard coded defaults. These variables control among other things the time and scale ranges for all graphic displays, the duration and frequency (interval) of the "Delta" pressure steps, and the solenoid control valves choices used during the pressure step phases of a test. An option for user configuration of these defaults was provided in the form of a separate text file containing "plain English" settings that can be loaded instead of the hard coded defaults. A default is only replaced if its "keyword" is found in the list shown in FIG. 7.1 Invalid "keywords" are ignored. The loading process continues until all text lines have been scanned. The user visual interface (displays) is now setup. It consists of a two page display screen. The first page displays all real-time data (i.e. IR signal, chamber pressure, elapse time, and valve settings) in numeric and graphical formats. A second page was devoted to close examination of the resultant "Delta" plot data used in water content assessment. Initialization for both screens consists of clearing all old data (displays prior to the programs execution) then drawing graphic screen boundaries and labeling numerical data print zones.

Internal program variables are now setup. Internal variable unlike those previously mentioned are for use by the program itself to remember event occurrences such are current graphic data plot locations or the availability of new data being. These variables are manipulated by the program based on timed events, preset conditions, or indirectly through user input in the command processing routine. Some examples of the later being pump status, data logging conditions, and auto-shutdown settings as will be seen in the breakdown of command functions.

The last setup function is initialization of the timed interrupt feature. The interval is set to 1 interrupt per second and the timer is started. The one second rate to give reasonable time resolution of test events without accumulating large amounts of data at an unnecessarily high rate.

An interrupt can be best described as a once a second distraction for the program. It occurs regularly while "Timer 1" is in an enabled state. It can occur during any one of the programs many steps. During this time period (which often lasts only 1/50th of a second or so) program control passes to the "Timer 1 Background Task" as shown in FIG. 7.7. Here, the remote unit in interrogated for the current values of the IR signal and chamber pressure sensors. This data is stored in temporary variables. If the data logging function has been enabled the new data is sent to the system disk. A status flag is set to tell the rest of the program that data is available.

Main Program Loop

The main program loop (FIG. 7.2), as mentioned earlier, has only two functions. First to display new data and second to process user commands. A third function "automation" appears when the feature is enabled from the relevant user command option.

Managing New Data

Each second of the program operation; data is being gathered from the remote unit. This data is then printed on page 1 as numeric values of temperature and pressure. A detailed chart-recorded like graph is also generated to allow the operator to see the last 5 min. of a run in great detail. A graph that runs for a time scale fixed in the default variables gives a total test view. The status of all digital control lines (pump, solenoid control valves, etc . . . ) is displayed. Should the automatic pressure step mode be enabled then the program will go to the pressure step management part of the program FIG. 7.6. If not the program goes on to look for a user keycode.

Command Processing

All commands are in the of a single letter. Each command has a different number of parameters accompanying it. FIGS. 7.3–7.5 show the flow for all the commands. The end of all command sequences (with the exception of the "Q" key) end by following the B path back to the main program loop.

Starting at FIG. 7.3 the first command group is the numbers "0–7" these correspond to the binary combination of solenoid control valves states, for example 0 will close all solenoid control valves while 2 would open solenoid control valves two. The status display for the solenoid control valves is updated each time one of these commands is used. The rest of the functions will be listed in order of appearance and their significance explained. The "A" key will toggle the two data display screens. During testing it was found that the characteristics of the "Delta" curve were of greatest relevance, so to enhance test control of full screen size graph was devoted to display of the "Delta" curve. One feature of using the "Delta" step values is that the polarity of the step will depend on the direction of the pressure step. The "B" key was included to switch the direction of this step mathematically by multiplying all "Delta" step points by −1, allowing the preservation of the shape of the curve as displayed on screen page 2. A pressure pulse is assigned a width (Duration) through the "D" key. This value is used by the auto-pulse mode. A simple way to stop a recording cycle is provided through the "E" key. This key shuts down the automatic data recording, opens all solenoid control valves, and stops the "Delta" pulse cycling. It then resumes normal display operation so that the depressurization of the chamber can be monitored for sample removal.

The first command shown in FIG. 7.4, the "I" key, is for setting the interval (repetition time) for a "Delta" pulse in the auto-pulse mode. A feature to allow for the ending of a test run at a precise elapsed time or "Delta" value without the need for constant supervision is activated by the "K" key. The exact functioning of this feature is explained in FIG. 7.6. The stopping value for the previously mentioned function is set by the "L" key. Here the option to stop in a specific value of the delta or after a specific value of elapse test time is entered. The "M" key toggles the auto-pulse mode on and off. This feature automatically steps the chamber pressure to produce the "Delta" values. Control of the systems vacuum pump is done through the "P" key. It controls a switched outlet provided for the pump.

A pressure step in the sample chamber is generated by switching different needle valves that act as controlled leaks. The values are controlled through the systems solenoid control valves bank which is directly accessible through the "0–7" keys. A step occurs when the system chooses a new value for the period of time specified with the "D" key. The solenoid control valves switched to during this cycle is set through the "S" key, which is the first command listed on FIG. 7.5. The pollen grains often adhere to each other or "clump together" during the drying process. A form of physical agitation is provided in the form of a low frequency 10–20 Hz magnetic field, which influences a permanent magnet mounted to the bottom of the sample chamber. This field is switched from the program using the "Z" key. The "R" key starts the data recording process. A file name which the data is stored under is entered here. Next the desired sample interval is entered. This has no affect on the 1 second data collection rate. Its primary function is to allow for recording at a rate longer than 1 second as the signal tends to have a rather relaxed rate of change and a very large amount of data would always have to be gathered if the rate was fixed. A written comment may also be added here to label the data. With this user input gathered the program attempts to setup required disk control parameters through the native operating system. An error at this point is handled through that system. Upon successful completion the run-time variables are reset and a test begins. The program continues from the keyboard scan module (B path). The last program command is the "Q" key this key stops the program. It first shuts off all sampling, closes any open data files, shuts off all control signals (opening solenoid control valves, shutting off pump etc.), and ending communication with the remote interface unit, control of the host computer is then turned over to the native operating system (DOS).

Automatic Operations

The specifics of the automated control and operation features are shown in FIG. 7.6. When the auto-pulse mode is enabled ("M" key) control is branched through the (D path) every time new data is received. Should a pressure pulse be currently in progress, the program will see if it is time to finish the step. A step is finished by gathering the current IR reading then switching the solenoid control valves selection back to the default value selected at the start of a test. The IR data in used together with IR data stored at the beginning of the pulse cycle to calculate the "Delta" value. This new data is displayed and graphed on screen page 2. Next, should the auto-run feature be active the new "Delta" value (or elapse time) will be compared to the stored stop point ("L" key) and if correct then the program follows the G path which executes the code also used by the "E" key. Had either the pulse length not exceeded the "duration" setting or the auto-run feature been off or the stop value not been reached yet then program execution would have followed the B path back to the keyboard test module. Upon entering the D path had a pulse not been active the program would determine if it where time to start one by comparing the "I" key interval setting with the elapse time. If the interval is a multiple of the elapse time a new pulse will start. The beginning of a pulse consists of first saving the IR value. The current solenoid control valves is switched to the one selected with the "S" key. The B path is then taken back to the keyboard scan module.

Turning to the solenoid control valves driver 80, contained within the computer interface unit 70, the gas solenoid control valves 82, 84, and 86 are interconnected by solenoid control valves connector 62 to the solenoid control valves driver 80. As mentioned above the pressure control box 40 contains three gas solenoid control valves 82, 84 and 86, respectively. Each of these solenoid control valves is connected to their respective needle valves 57, 59, 61 which are each connected to line 63 which passes through particle filter 44 and vents to the open atmosphere at vent 123. The three needle valves 57, 59 and 61 are adjustable respectively through first needle value adjuster 67, second needle valve adjuster 69 and third needle valve adjuster 71. These adjustments permit a controlled leak out of the sample chamber 20 which allows the chamber 20 to have a set pressure. Each needle valve 57, 59 and 61, have a respective solenoid control valves that is switched by the computer interface unit 70. In operation of the present invention two of the solenoid control valves are utilized so that a leak value for two of the respective valves is adjusted to allow pressure levels to be stepped in intervals by switching between the valve selections. The remaining valve is adapted to allow a gradual repressurization of the chamber to prevent sample scatter.

In FIG. 5 a cross-sectional view of the sample chamber 20 is depicted. The sample chamber 20 is constructed from a standard aluminum alloy (T6061) and has no surface finish. In the exemplary embodiment of the present invention, a thermopile element 26 is used as the temperature sensor 22 based on the established relationship between black body emissions and an object's temperature. The thermopile element (infra-red temperature sensor) 26 is mounted to the removable lid 18, with its signal wires 15 brought through the top with the vacuum feedthroughs 16. The thermopile amplifier 87, in the microprocessor 72, is interconnected with the temperature sensor 22 in the lid 18 of the sample chamber 20. The thermopile element 26 is adapted to be press fitted with the upper rim of the chamber for optimum thermal contact. A single "O" ring provides the vacuum seal between the lid 18 and the sample chamber body 17 of the sample chamber 20. The sample receptor 21 is positioned within a mechanically isolated platform 6. Rubber pads 1 provide the isolation between the lip 11 of the platform 6 and the sill 13 within the chamber wall 12. Directly below the sample receptor 21 and opposite of the thermopile element 26 is the bottom wall 112. Attached proximate to the bottom wall 112 is the magnetic agitator 24. A small electromagnet 106 is attached to the bottom wall 112. Directly below magnet 106 there is a coil wire port 109 that goes through the chamber wall 12. The coil wire port 109 that goes directly through the sample chamber body 17 to the interior chamber wall 14 for connection with the magnetic agitator 24. A vacuum port 110 likewise extends from the interior 8 through the interior chamber wall 14 through sample chamber body 17. The vacuum line 42 is connected thereto. The vacuum port 110 is positioned below the sample receptor 21 to avoid sample scatter when applying a vacuum into sample chamber 20. The sample receptor 21 is a small plastic cuvette adapted to maintain the pollen therein.

In operation, then the present invention reduces the relative water content of pollen placed within the sample chamber. The pollen is subjected to reduced atmospheric pressures. In the preferred embodiment of the present invention the pollen is subjected to stepping of pressure levels. In other words, the pressure is reduced from atmospheric pressure to a first pressure level and then the pressure is changed to a second pressure level. This repeated changing between the first and second pressure level is herein defined as stepping.

Broadly, then, the present method of the invention for preparing pollen for storage comprises four basic steps: selecting pollen having a first moisture level; exposing the pollen to reduced atmospheric pressure; reducing the first moisture level of the pollen to a second moisture level; and storing the pollen having the second moisture level. In operation then the previously described device is used in the following manner.

Pollen is extracted from the plant. In the preferred method of the present invention, pollen is extracted from a single tassel of maize. The pollen can be conditioned to remove any debris that may be present such as anther debris. The pollen is then placed into or on the sample receptor. Therefore, the sample receptor should be handled with forceps. Using the forceps or tweezers, the sample receptor which contains the pollen is placed into the sample chamber. The lid of the sample chamber is secured. The lid contains a flexible sealing element to engage the chamber body. This sealing element permits the vacuum to be readily created within the chamber. Next the sample chamber is allowed to equilibrate to room temperature. When the temperature sensor has reached equilibration, the value of the temperature is set to net zero. As clearly shown in FIG. 1, the computer interface unit 70 has two primary adjustment knobs present. One is the infrared signal gain. And the other is the infrared signal zero. The infrared signal zero should be set when the chamber 20 has been equilibrated.

At this point if the apparatus is set up for general data collection, the sampling interval for this data collection can be selected. Alternatively, the device can simply be turned on, programmed to run until a selected delta value is reached. When the temperature is equilibrated and the apparatus is set to net zero, then the magnetic agitator is switched on. This, of course, agitates the pollen within the sample receptor inside the sample chamber. The solenoid control valves are open. The vacuum pump is engaged so that the pressure in the sample chamber is reduced. The reduction of the pressure in the sample chamber to a level which is between 5 and 30 Torr at intervals of approximately 120 seconds. It should be understood by a person of ordinary skill in the art that the interval time period can vary. At repetitive intervals of somewhere between 30 seconds and approximately 200 seconds, preferably 120 seconds, the pressure within the sample chamber is reduced. The length of each pressure step may be less than the modulation interval setting. The set modulation pulse width is approximately ⅛ of the modulation interval. The pressure is pulsed with or reduced with in a pressure step approximately to a level lower than the previous level. The difference between levels can be as great as a 20 Torr difference but between 15–5 Torr with 10–7 Torr being preferred between the two pressure levels. There can be a 1 Torr difference if the delta change in the temperature remains measurable, however this will substantially increase the time. The difference between the levels of pressure can be selected by determining the sensitivity to moisture extraction of the specific genotype of the pollen selected for cryopreservation. Most pollen from various maize genotypes which has been extracted from a single tassel can remain viable at a 5 to 10 Torr pressure reduction. The repetitive pulsing or stepping of the pressure in the sample chamber causes the water to be extracted from the pollen of the single tassel.

The loss of moisture from the pollen from the first moisture level ultimately to a second moisture level in a stepwise manner causes a gradual temperature change in the sample chamber. The sample chamber temperature change is recorded by the temperature sensing device, often an infra red sensor. The repeated pulsing of the pressure gives rise to a modulated temperature signal, if the device is sampling the data at intervals. The difference in temperature between the two pressure settings at any given time is representative of the relative amount of water lost within the pollen in the sample receptor in the sample chamber during the pressure pulse. When the differences in temperature between the two settings is given in time intervals and plotted, the kinetics of temperature change due to water loss follow a set pattern as shown in the Figures. The delta plot reaches a plateau (less then 12% moisture content and preferably less than 10%), which with a 10 Torr difference between pulsing levels of 10 Torr & 20 Torr often happens after a period of 120–150 minutes (this time period can vary based on genotype of pollen and initial moisture level of the pollen sample). This delta indicates the pollen has reached the correct level of drying required to maintain viability after storage at either −70° C. or −196° C.

Figure 8:
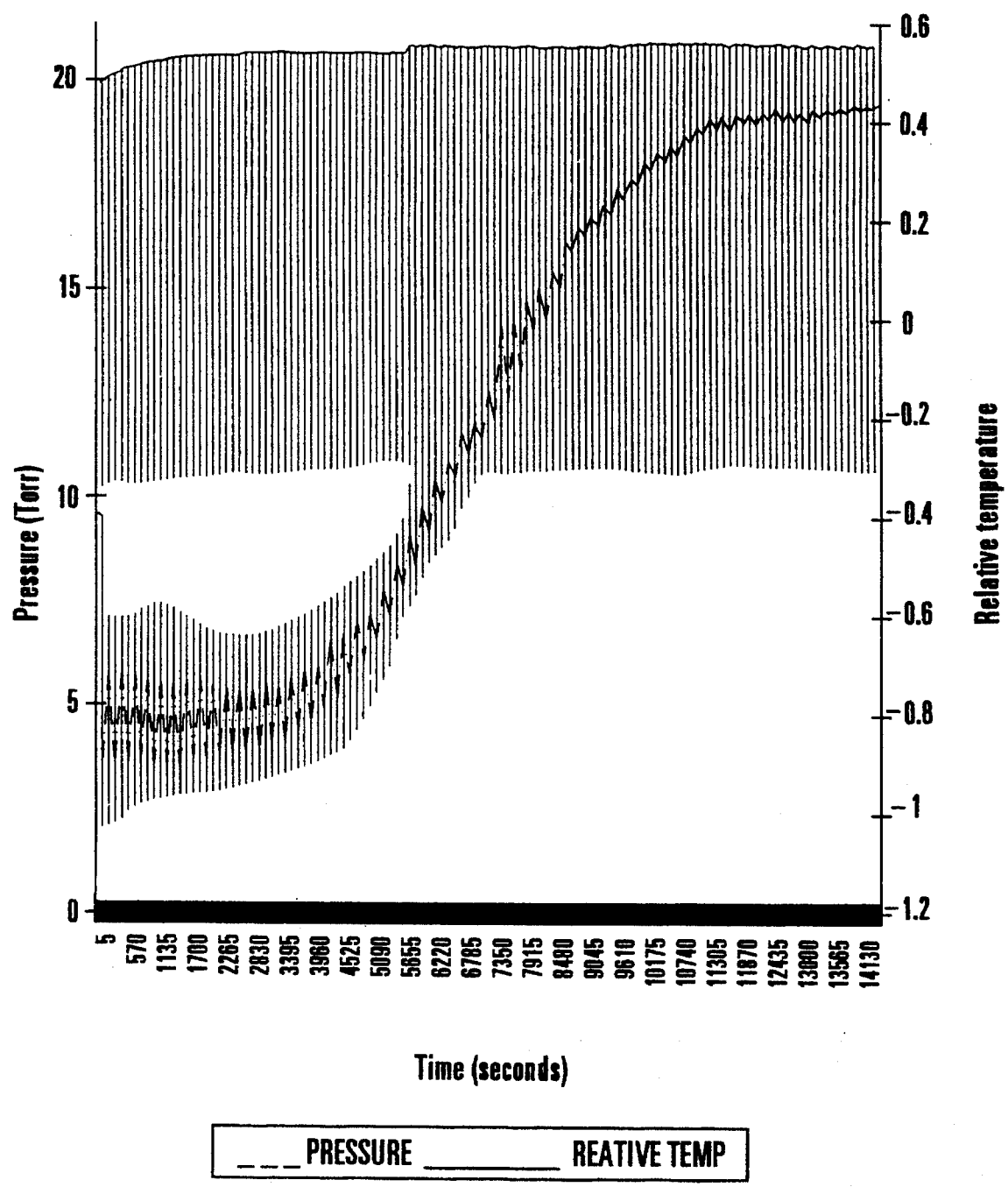
FIG. 8 is a graph which demonstrates the effect of pressure pulsing treatment on the infra red signal from a pollen sample over a 4 hour drying period.

The combination of reduced pressure and pressure pulsing causes water to evaporate from the pollen sample. This loss of water causes a temperature change in the pollen sample. Using the infra-red temperature sensor (thermopile), the changes in temperature of the pollen sample are measured accurately. This measurement reflect both the magnitude and rate of water loss from the sample. The use of a pressure pulse every 120 seconds allows an estimation of the water loss from the sample at any time during the drying process. Turning to FIG. 8, this figure demonstrates the effect of the pressure pulsing treatment on the pollen as evidenced by the change in the infra red signal from a pollen sample over a 4 hour drying period. Clearly, the magnitude of the infra-red pulses declines over time, and the trace begins to reach a plateau after approximately 4 hours.

Figure 9:
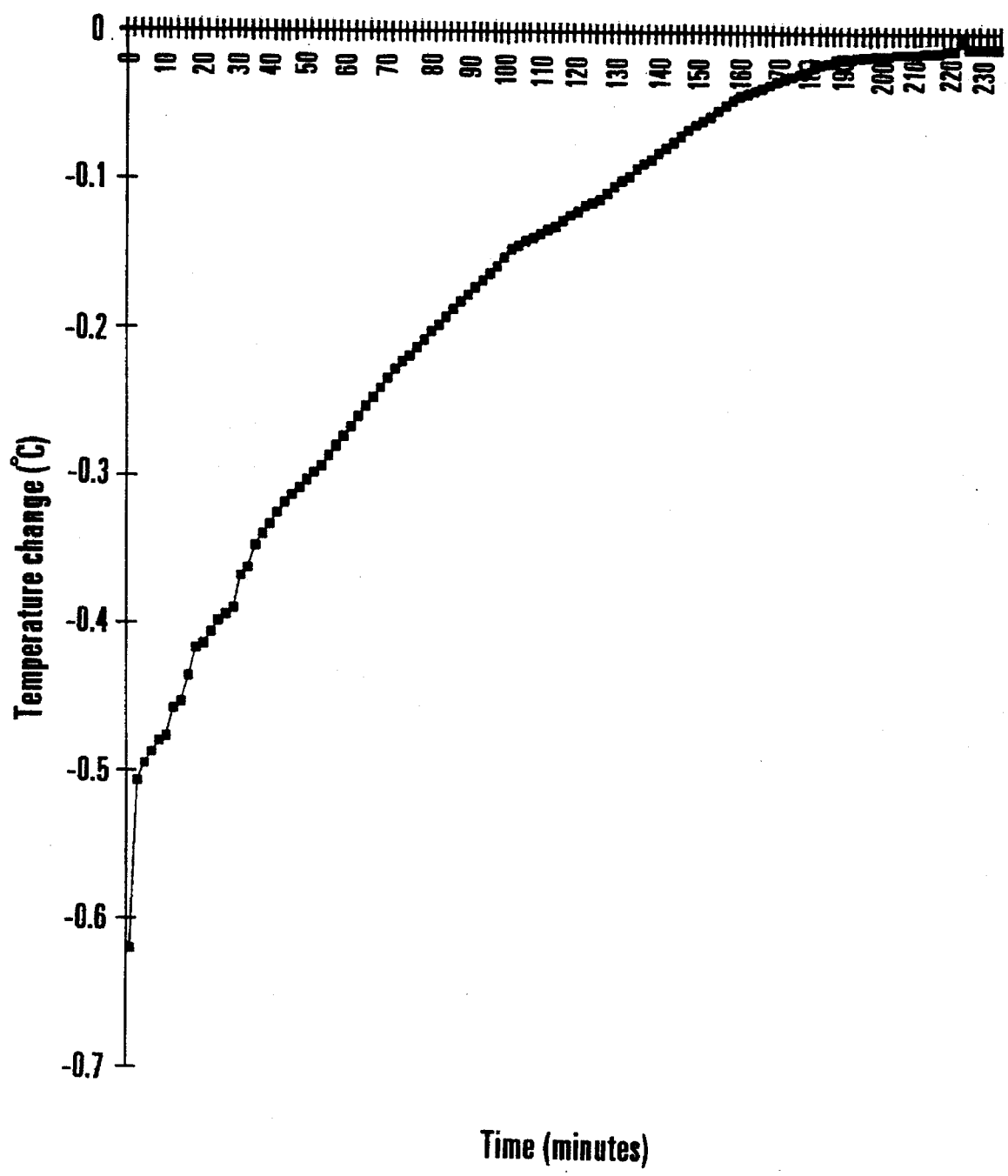
FIG. 9 is a graph which shows the magnitude of the infra-red pulses termed "delta"; the graph shows changes in infra-red pulse magnitude from a pollen sample of the inbred line A, over time using a pressure step system of 20/10 Torr.

As can be seen from FIG. 9, there is a rapid rise in delta over the first 8 minutes, followed by a gentler curvilinear rise over the next 192 minutes, followed by the onset of a plateau after approximately 200 minutes. FIG. 9 was developed from experiment number one which follows.

Figure 10:
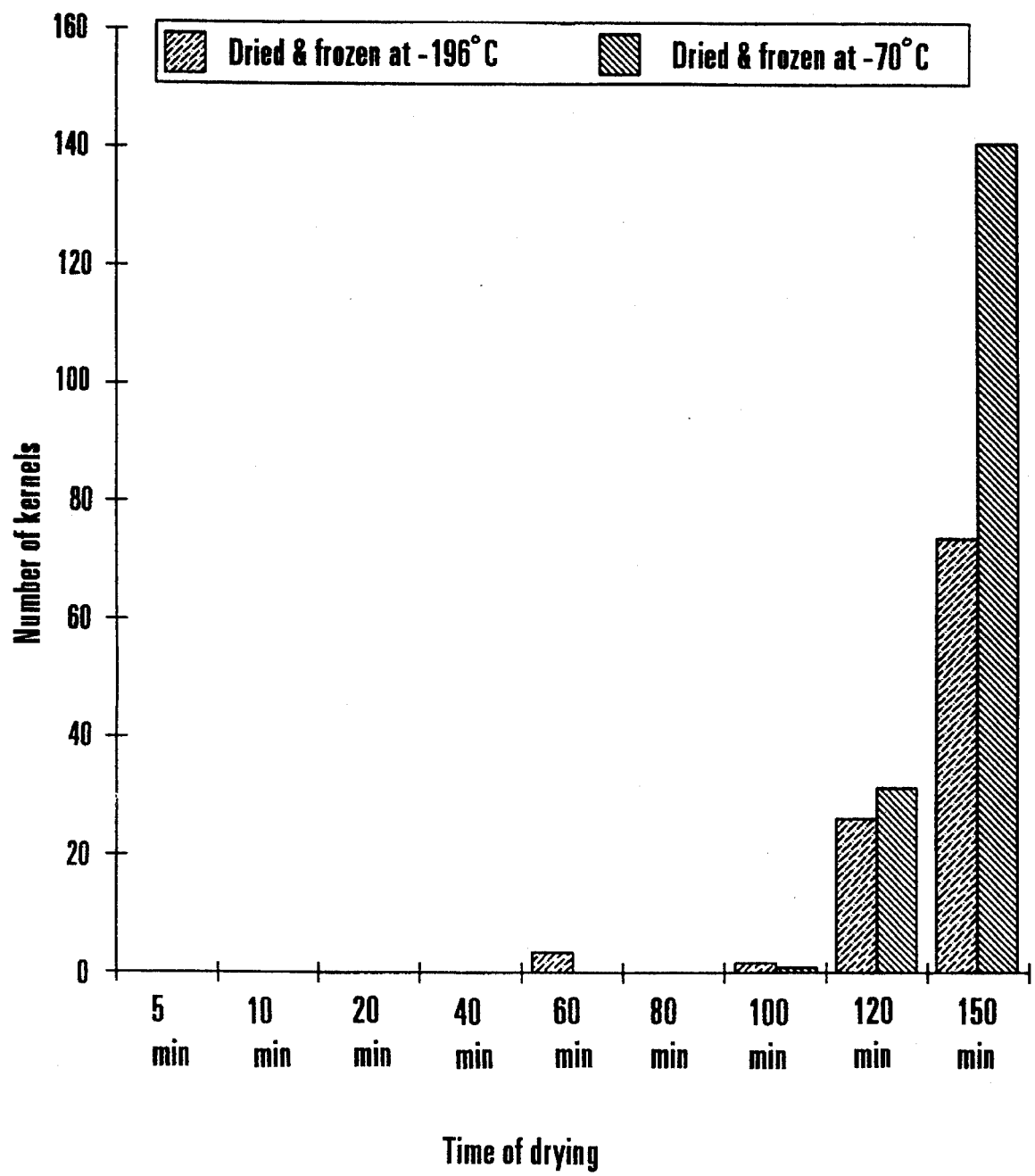
FIG. 10 is a graph which shows the effect of drying time at a pressure setting of 20/10 Torr on seed set following freezing at either −70° C. or −196° C. and subsequent recovery.

FIG. 10 shows the effect of the vacuum pressure on the pollen. The graph shows the effect on the pollen of a pressure setting of 20/10 Torr on seed set following freezing at either −70° C. or −196° C. and subsequent recovery. Recovery meaning the viability of the cryogenically preserved pollen. Clearly, pollen dried for the longest period of time resulted in the greatest seed set capability following freezing and subsequent rewarming.

In an attempt to calibrate the infra-red delta signal, relative water content was measured following drying over a series of delta points at a pressure setting of 25/15 Torr. The data presented in FIG. 11 describes a close correlation ($R^2=0.9186$) between the delta value and relative water content of pollen samples following drying. Thus, the delta value provides a unique estimation of relative water content which can be used to estimate the point at which pollen can be removed from the chamber an stored cryogenically while maintaining viability.

A pressure setting of 20/12 Torr, identified a "window" of both delta (−0.04 to 0.045) and relative water content (6.5–10.0%) which results in readily cryogenically storable pollen. Cryopreserved pollen from various inbred lines representing 3 of the 5 heterotic groups of maize have been tested and found viable after storage using these windows.

Figure 13:
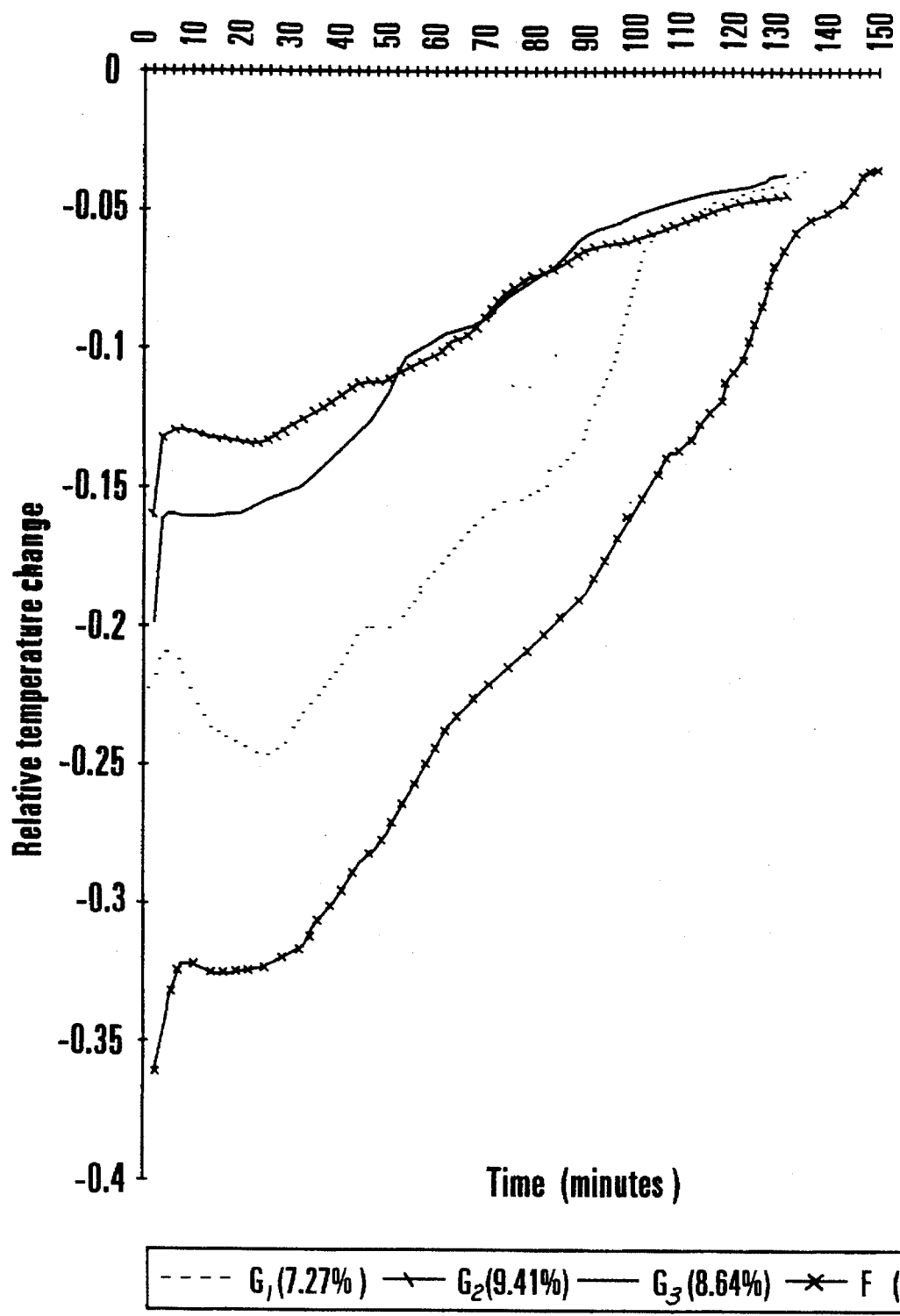
FIG. 13 is a graph which shows four different delta plots, of pollen from individual plants.

The data presented in FIG. 13 shows four different delta plots, three of which are from pollen from individual plants of the same inbred line. The fourth plot is from a individual segregant from a backcross population. Clearly, both the starting delta's (which are indicative of initial relative water contents) and the time taken to reach a delta value of between −0.04 and −0.045 are different for each individual pollen sample. Initial relative water contents for all 4 pollen samples are presented on the left side of the graph. As can be seen, the initial RWC for the 4 plants was different, ranging from 34.95% to 43.05%. The resulting relative water contents were between 6.93% and 9.41% and all four pollen samples produced viable seed following storage at −196° C. in the vapor phase of liquid nitrogen and subsequent rewarming prior to pollination (Table 1). Clearly, the delta value provides a most effective method for estimating the relative water content (RWC) required for successful cryopreservation.

EXAMPLE 1

The apparatus employed was described above. In the present experiment this apparatus was interfaced with a computer. The controlling program for the apparatus was on the hard drive of the computer. The software employed follows the decision flowchart listed above. To clearly explain the procedure the program control keys of the computer program are listed. The control key is key Q. It exits the program. The Q control key closes all data files and causes the program to go back to DOS on the computer. This key turns off the vacuum pump and all solenoid control valves. This function was used after the system had been shut down with the "E" function during the normal test run. Program control key for ending the test run was "E". The function of control key "E" was to close down a sample run without exiting the program between samples. It shuts down the current test, closes all data files, allows the chamber to be brought back to room temperature and the program goes back to data screening mode.

Control Key R—Starts a Recorded Test

Control key R sets up the system for a sample run. The program asks for a file name. The name is used in the program for the raw data and the delta curve. This key requires the space between the sample points (in seconds).

Control Key I—Set Modulation Interval

This control key I sets the spacing between each pressure step. The units are in seconds, in this program the spacing should not bet set for an interval of less than 30 seconds as this confuses the delta plot. The default in this program is 120 seconds.

Control Key D—Set Module Pulse Width

Control Key D sets length of the pressure set. This was in seconds. In this program the length of the pressure set should be less than the modulation interval setting. The length of the pressure set was usually approximately ⅛ of the modulation interval. The computer set the default at 15 seconds.

Control Key S—Set Step Solenoid Control Valves

Control key S chooses which solenoid control valves will be switched to during the module interval. The range is 0–7 and is the same as the manual control valves. The computer set the default at 1.

Control Key M—Toggle Modulation Mode

Control key M switches the modulation feature on and off. The status shown in the lower right hand corner of the screen.

Control Key P—Toggle Pump

This key toggles the key on and off. This amounts to switching the relay located in the silver box that the pump is to be plugged into.

Control key Z—Toggle Magnetic Shaker

Control key Z toggles the magnetic shaker on and off.

0–7 Select a Solenoid Control Valves Group

Each of the numbers 0–7 correspond to a specific binary combination of pressure bleeding solenoid control valves. One is the lowest setting (about 5 Torr). Two in this computer system is a next pressure up about 10 Torr. And the last one is set for re-pressurizing the chamber to approximately 70 Torr.

After the control key R which starts a test was selected, the computer asked for a file name. There are basically two types of files: one to store the test pressure, temperature, and time; the other to store the modulated delta data. There is a large difference in sample rates for raw data and deltas. Both of these files were output in a format that was compatible with EXCEL.

Using the above described computer functions, the following process was performed. Prior to the use the sample cuvette was washed, dried by hand, placed in the chamber and pumped down for a few minutes to ensure it was dry. The chamber was prepared by pumping it down with an empty sample receptor to a zero value with all needle valves closed. The apparatus was allowed to run for fifteen minutes to clear any moisture that had accumulated in the tubing. At the end of the fifteen minute period, the IR reading was reset to 0. Then the vacuum pump was shut down and the sample chamber was re-pressurized. Because the system is a vacuum evaporation system, the rate of water removed from the chamber is measured by the sample temperature drop. Therefore, it is imperative that heat is not added to the sample, the sample holder, or surrounding chamber. The sample receptor was handled with tweezers at room temperature. The lid of the sample chamber was held only as long as necessary to insert the sample receptor into the sample chamber.

The vacuum was switched on and the pressure settings were adjusted (valve 1 was set at 20 Torr and valve 2 was set at 10 Torr). The pollen sample was collected from the greenhouse. The pump was switched off and the chamber was vented to atmospheric pressure by pressing control key E. The pollen was sieved on aluminum foil to remove anther debris. The sieved pollen was poured into a small 1.8 ml vial and it was transferred into the sample receptor. The sample receptor was handled with forceps at all times. The receptor was placed within the sample chamber. The receptor was placed into the sample chamber and the sample lid was tightly secured onto the sample chamber. The chamber was allowed to equilibrate. When the temperature reading equalized, the value was set to zero. The following data was inputted into the computer, the filename, the label and the sample rate. The sample interval for data collection was usually between 2–4 seconds. The magnetic agitator was switched on using control key Z. The solenoid control valves were all open at this point. The switch on the pump was placed on. In about 10 seconds the chamber pressure dropped to below 100 Torr and the second valve was selected. By pressing control key M the modulation was switched on and it automatically dropped the chamber pressure to the selected Torr for fifteen minutes in 120 second cycles.

The system was permitted to run and was stopped when the delta reaches –0.05 on the delta scale. This was prior to reaching the plateau and corresponds approximately to relative water content of between 12 and 15 percent. The run was completed by pressing the E key which switches off the pump and vents the chamber. The chamber was allowed to equibalate to room temperature and the sample was removed. The samples were placed in appropriate storage (–70° C. and –196° C.). Half of the pollen was immediately frozen at –70° C. in a freezer, the other half was placed in vapor phase of liquid nitrogen at –196° C.

EXAMPLE 2 an inbred line A was dried in the cryo-prep the method described above, for 5, 10, 20, 40, 60, 80, 100, 120 and 150 minutes. The pulse interval for this initial experiment was 120 seconds. Each run was conducted on a separate day, and pollen was collected at 8.30 am each morning. The pollen was sieved and then divided into four equal amounts: (1) pollen that was immediately used for pollination in order to check the viability of the pollen sample; (2) pollen that was frozen immediately in either a –70° C. freezer or in the vapor phase of liquid nitrogen at –196° C.; (3) pollen that was dried in the cryo-prep chamber and then immediately used for pollination; (4) pollen that was dried and immediately frozen in either a –70° C. freezer or in the vapor phase of liquid nitrogen at –196° C. The data presented in FIG. 13 shows four different delta plots, three of which are from pollen from individual plants of the same inbred line. The fourth plot is from a individual segregant from a backcross population. Clearly, both the starting delta's (which are indicative of initial relative water contents) and the time taken to reach a delta value of between –0.04 and –0.045 are different for each individual pollen sample. Initial relative water contents for all 4 pollen samples are presented on the left side of the graph. As can be seen, the initial RWC for the 4 plants was different, ranging from 34.95% to 43.05%. The resulting relative water contents were between 6.93% and 9.41% and all four pollen samples produced viable seed following storage at –196° C. in the vapor phase of liquid nitrogen and subsequent rewarming prior to pollination (Table 1). Clearly, the delta value provides a most effective method for estimating the relative water content (RWC) required for successful cryopreservation.

Pollen samples 2 and 4 were exposed to extreme freezing temperatures for a period of one hour. They were then rapidly thawed by placing the storage vials into a beaker of water which had been maintained at 25° C., and allowed to re-hydrate on the silks following pollination.

In all cases, fresh pollen which was immediately used for pollination, produced kernels on an ear that was pollinated. Furthermore, all pollen that was dried only, and then used for pollination, regardless of the drying time, produced kernels on an ear that was pollinated. This demonstrates that the drying process did not reduce pollen viability per se. In marked contrast, pollen that was immediately frozen either at –70° C. or at –196° C. produced no kernels upon pollination. This clearly indicates that without adequate water removal, pollen that is exposed to extreme freezing temperatures, loses all viability and is unable to successfully fertilize egg cells. However, the data presented in FIG. 9 clearly demonstrates the utility of the pollen cryopreservation method and apparatus in removing water from pollen to a point at which pollen can successfully withstand exposure to the extreme freezing conditions of –70° C. and –196° C. The data presented in FIG. 10 clearly shows that pollen dried for either 5, 10, 20, 40 and 80 minutes, was killed on exposure to the freezing temperatures. Drying times of 60 and 100 minutes appeared to show some pollen survival. In marked contrast, pollen dried for periods of 120 and 150 minutes produced kernels following pollination, with the drying time of 150 minutes providing the maximum viability at either –70° C. or –196° C.

EXAMPLE 3

This experiment was designed to assess the correlation between the delta value from the infra-red signal and the relative water content of pollen after drying in the sample chamber. A pressure setting of 25/15 Torr was used in this experiment. Pollen from an inbred line A was dried in the invention described above, and removed at a range of delta values from approximately −0.01 to approximately −0.07. The pulse interval for this initial experiment was 120 seconds. Each run was conducted on a separate day, and pollen was collected at 8.30 am each morning. Relative water content was calculated for each pollen sample after drying in the sample chamber using the equation described below:

$$RWC\% = \frac{\text{chamber-dried pollen weight} - \text{oven-dried pollen weight}}{\text{chamber-dried pollen weight}} \times 100$$

Figure 11:
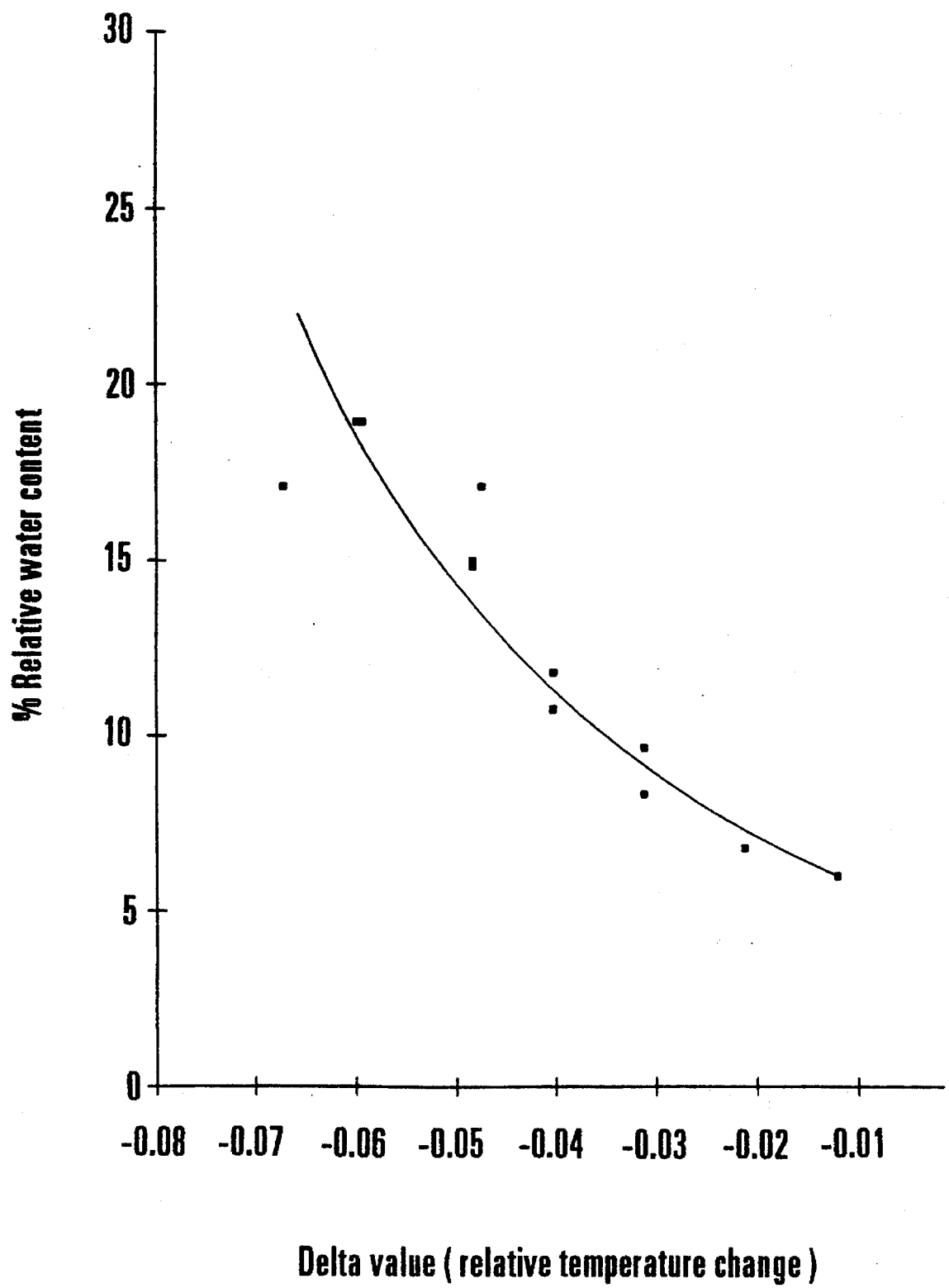
FIG. 11 is a graph which shows a close correlation ($R^2=0.9186$) between the delta value and relative water content of pollen samples following drying (relative water content was measured following drying over a series of delta points at a pressure setting of 25/15 Torr).
Figure 12:
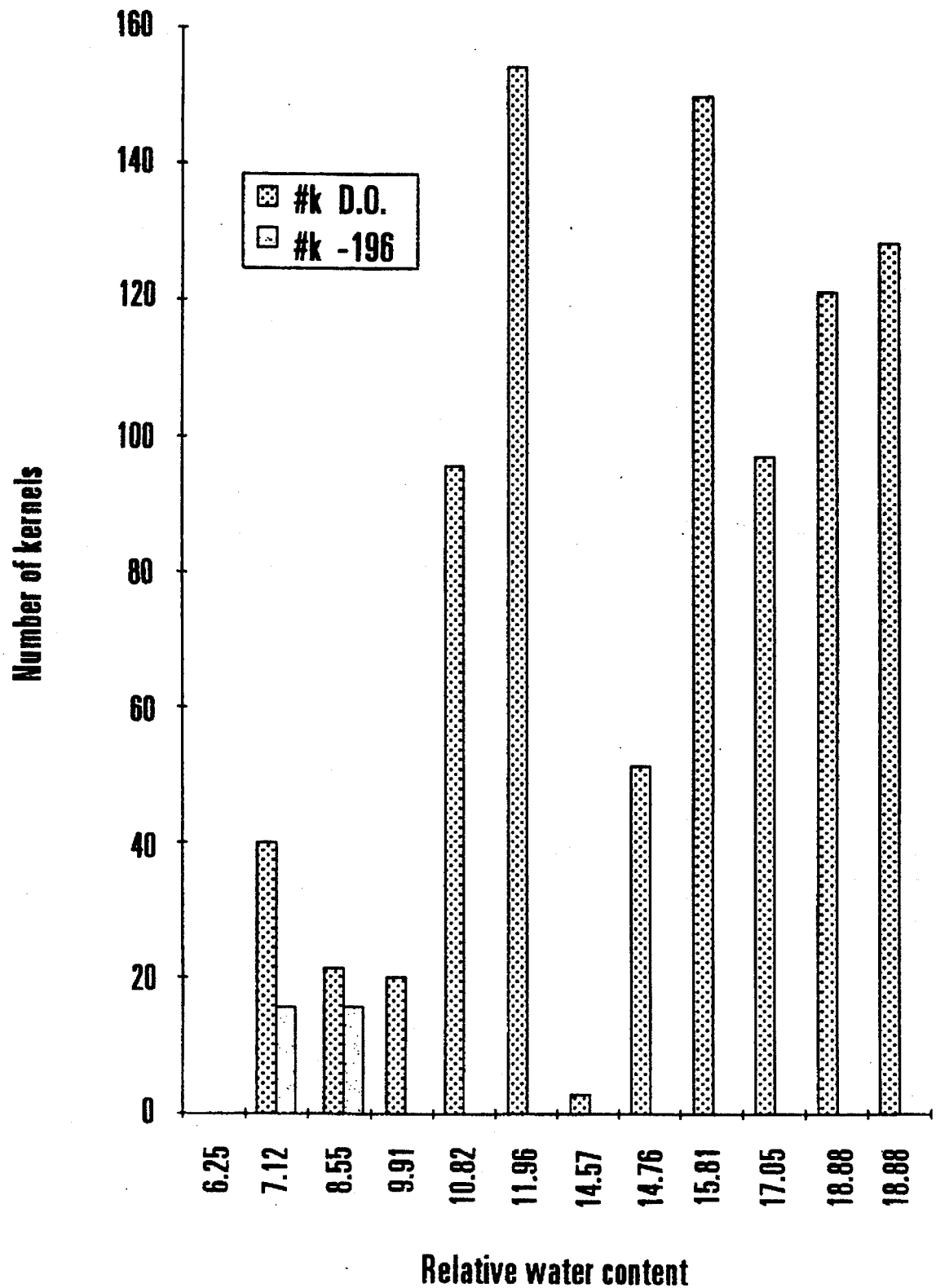
FIG. 12 is a graph which shows the relationship between relative water content (also drying only (D.O.) and drying followed by freezing at −196° C.), and viable kernels following pollination. The graph shows the effect of larger drying period which results in lower RWC on the viability of dried only pollen.

The data presented in FIG. 11 shows the close correlation ($R^2 = 0.9186$) between delta value (derived from the infra-red signal), and relative water content of pollen dried in the cryo-prep chamber. Clearly, the delta value can be used to estimate relative water content. In this same experiment, cryo-preservation was achieved with pollen dried to between 7% and 9% relative water content. This pollen was stored for 48 hours at −196° C. However, the gentler drying pressure increased the time required for drying by up to 100 minutes. This, in turn reduced the viability of dried only pollen (FIG. 12). It was clear from this data that drying time also affects the ability to obtain viable pollen for cryo-preservation. A pressure setting of 20/12 Torr was subsequently chosen in order to reduce the drying time, and this experiment is described below.

EXAMPLE 4

In this experiment, a pressure setting of 20/12 Torr was used in order to speed up the drying process. Pollen from 3 different plants from genotype G and 1 plant from genotype O were collected in the above manner. The pollen was sieved and then divided into four equal amounts: (1) pollen that was immediately used for pollination in order to check the viability of the pollen sample; (2) pollen that was frozen immediately; (3) pollen that was dried in the cryo-prep chamber and then immediately used for pollination; (4) pollen that was dried and immediately frozen in either a −70° C. freezer or in the vapor phase of liquid nitrogen at −196° C. By closely monitoring the pollen of the selected genotype by the difference in temperature between the two pressure settings over time to note the plateau period, permitted the drying level of the genotype of these specific pollen samples (and any pollen samples). The "window" necessary to reach the correct level for cryopreservation of any genotype is determinable without undue experimentation. Thus, the potential differences in the water loss from pollen grains having different genotypes can be overcome by analyzing the data produced by the present system.

After the pollen is prepared for cryogenic preservation it can be categorized and given a symbol that corresponds to the parent plant or an designation that permits the pollen to be identified and selected for future use. The tagged pollen is stored in the vapor phase of liquid nitrogen. General methods of storage in the vapor phase of liquid nitrogen is known to those skilled in the art of cryopreservation. When tagged pollen is selected for breeding purposes it is withdrawn from the vapor phase and allowed to rehydrate. The rehydration can occur on the silks of the plant which is being bred. The pollen can be rehydrated prior to being placed on the silks of the receiving plant or plants. This pollen bank can be remote from the receiving parent. The preserved pollen can be shipped in dry ice and used to pollinate plants anywhere.

TABLE 1

| Seed set from cryo-preserved pollen. | | |
|---|---|---|
| Plant | RWC/Pollen | Seed Set |
| GE92512 | 7.27% | 42 |
| GE92513 | 9.41% | 54 |
| GE925132 | 8.64% | 34 |
| OF225172 | 6.93% | 52 |

EXAMPLE 5

The same protocol as described in example 1 was preformed using a step of only 5 Torr, however the range was pulsing between 10 Torr and 5 Torr. This pulsing range worked more quickly then did the other higher ranges. This range did not result in viable kernels after storage in the vapor phase of liquid nitrogen. This range was not tolerated well by all genotypes of pollen. Thus the preferred range for preparation for storage in a germplasm bank is 20 Torr −12 Torr.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A method of preparing pollen for storage, wherein the moisture level of the pollen is reduced to a second moisture level wherein substantial viability of the pollen during Storage is maintained, said method comprising the steps of:

(a) selecting pollen having a first moisture level;

(b) exposing said pollen having a first moisture level to reduced atmospheric pressures;

(c) monitoring by an indirect, remote sensor, the moisture level of said pollen wherein a selected second moisture level can be identified;

(d) reducing the first moisture level of said pollen to a second moisture level; and (e) storing in storage said pollen having said second moisture level.

2. A method of according to claim 1 further comprising the step of monitoring the temperature of said pollen to determine when said first moisture level has been reduced to said second moisture level.

3. A method according to claim 2 wherein said monitoring is done by a heat sensitive detector.

4. A method according to claim 3 wherein said heat sensitive detector is an infrared detector.

5. A method according to claim 2 wherein said temperature is detected by the infrared rays.

6. A method according to claim 1 wherein said reduced atmospheric pressures range between 5 torr and 30 torr.

7. A method according to claim 1, futher comprising the step of reducing said atmospheric pressures to a first pressure for a selected first time period and increasing said atmospheric pressure from said first pressure to a second pressure for a selected second time period.

8. A method according to claim 7 wherein said first pressure is not more than 25 torr.

9. A method according to claim 8 wherein said second pressure is not more than 45 torr.

10. A method according to claim 7 wherein said first time period is five seconds.

11. A method according to claim 1 futher comprising the steps off:
(f) identifying a plant source of said pollen in storage; and
(g) categorizing said pollen in storage.

12. A method according to claim 11 futher comprising the step of repeating steps a–g wherein forming a germplasm bank having pollen which can be employed to pollinate.

13. A method of reducing the water content of pollen to a storage safe level wherein the water content of said pollen is such that the pollen can be stored for extended periods of time with limited decrease in pollen viability, the method including the steps of:
(a) exposing said pollen having a first moisture level to pulsed reductions and increases in atmospheric pressure resulting in a reduced atmospheric pressure adapted to decrease the first moisture level of said pollen;
(b) monitoring the decreasing moisture level of said pollen; and
(c) removing the pollen from the reduced atmospheric pressure when said moisture level is at a level that permits viable storage of said pollen.

14. A method according to claim 13 wherein said pollen is of Gramineae.

15. A method of preparing maize pollen for storage in a viable state, said method comprising the steps of:
(a) exposing maize pollen to reduced atmospheric pressure;
(b) monitoring a water content of the maize pollen indirectly, such that there is no loss of maize pollen and a safe level of water content is identified; and
(c) removing said maize pollen from said reduced atmospheric pressure when said water content of said maize pollen is at the identified safe level for long term storage of maize pollen in a viable state.

16. A method according to claim 15 wherein said reduced atmospheric pressure is pulsed.

17. A method according to claim 15 wherein said monitoring indirectly of said water content is performed by measuring relative temperature of said maize pollen.

* * * * *